US010494418B2

(12) United States Patent
Küry et al.

(10) Patent No.: US 10,494,418 B2
(45) Date of Patent: *Dec. 3, 2019

(54) IGG STIMULATED REMYELINATION OF PERIPHERAL NERVES

(71) Applicants: Baxalta Incorporated, Bannockburn, IL (US); Baxalta GmbH, Zug (CH)

(72) Inventors: Patrick Küry, Düsseldorf (DE); Nevena Tzekova, Düsseldorf (DE); Hans-Peter Hartung, Düsseldorf (DE); Corinna Hermann, Vienna (AT); Birgit Maria Reipert, Deutsch-Wagram (AT); Hans-Peter Schwarz, Vienna (AT); Hartmut Ehrlich, Vienna (AT); Sebastian Bunk, Vienna (AT)

(*) Notice: Subject to any disclaimer, the term of this patent is extended or adjusted under 35 U.S.C. 154(b) by 0 days.

This patent is subject to a terminal disclaimer.

(21) Appl. No.: 15/798,313

(22) Filed: Oct. 30, 2017

(65) Prior Publication Data
US 2018/0291087 A1    Oct. 11, 2018

Related U.S. Application Data

(60) Continuation of application No. 14/625,542, filed on Feb. 18, 2015, now Pat. No. 9,834,593, which is a division of application No. 13/781,283, filed on Feb. 28, 2013, now Pat. No. 8,986,670.

(60) Provisional application No. 61/605,117, filed on Feb. 29, 2012.

(51) Int. Cl.
*A61K 45/06* (2006.01)
*C07K 16/06* (2006.01)
*A61K 39/395* (2006.01)
*A61K 39/00* (2006.01)

(52) U.S. Cl.
CPC ........ *C07K 16/06* (2013.01); *A61K 39/39516* (2013.01); *A61K 45/06* (2013.01); *C07K 16/065* (2013.01); *A61K 2039/505* (2013.01)

(58) Field of Classification Search
None
See application file for complete search history.

(56) References Cited

U.S. PATENT DOCUMENTS 8,414,888 B2    4/2013 Fehlings et al.

FOREIGN PATENT DOCUMENTS

| CA | 2330170 C    | 11/2010 |
| EP | 2484381 A1   | 8/2012  |
| JP | 2003-70465 A | 3/2003  |

OTHER PUBLICATIONS

Asakura, K. et al., "Targeting of IgMκ Antibodies to Oligodendrocytes Promotes CNS Remyelination," *The Journal of Neuroscience*, Oct. 1, 1998, vol. 18, No. 19, pp. 7700-7708.

Bhatheja, K. et al., "Schwann cells: Origins and role in axonal maintenance and regeneration," *The International Journal of Biochemistry & Cell Biology*, 2006, vol. 38, pp. 1995-1999.
Bieber, A. et al., "Antibody-mediated remyelination: relevance to multiple sclerosis," *Multiple Sclerosis*, 2000, vol. 6, Suppl 2, pp. S1-S5.
Bieber, A.J. et al., "Human Antibodies Accelerate the Rate of Remyelination Following Lysolecithin-Induced Demyelination in Mice," *Glia*, 2002, vol. 37, pp. 241-249.
Buchwald, H. et al., "Long-term, continous intravenous heparin administration by an implantable infusion pump in ambulatory patients with recurrent venous thrombosis," *Surgery*, 1980, vol. 88, pp. 507-516.
Burstyn-Cohen, T. et al., "Accumulation of F-Spondin in Injured Peripheral Nerve Promotes the Outgrowth of Sensory Axons," *The Journal of Neuroscience*, Nov. 1, 1998, vol. 18, No. 21, pp. 8875-8885.
Colover, J., "Polyneuropathy in type 2 diabetes mellitus," *The Lancet*, Dec. 15, 2001, vol. 358, p. 2086.
Donofrio, P.D., "Immunotherapy of Idiopathic Inflammatory Neuropathies," *Muscle & Nerve*, Sep. 2003, vol. 28, pp. 273-292.
During, M.J. et al., "Controlled Release of Dopamine from a Polymeric Brain Implant: In Vivo Characterization," *Ann Neurol*, 1989, vol. 25, pp. 351-356.
England, J.D. et al., "Peripheral neuropathy," *The Lancet*, 2004, vol. 363, pp. 2151-2161.
Feasby, T. et al., "Guidelines on the Use of Intravenous Immune Globulin for Neurologic Conditions," *Transfusion Medicine Reviews*, Apr. 2007, vol. 21, No. 2, Suppl 1, pp. S57-S107.
Gabreëls-Festen, A. et al., "Hereditary Demyelinating Motor and Sensory Neuropathy," *Brain Pathology*, 1993, vol. 3, pp. 135-146.
Heinen, A. et al., "The cyclin-dependent kinase inhibitor p57kip2 is a negative regulator of Schwann cell differentiation and in vivo myelination," *PNAS*, Jun. 24, 2008, vol. 105, No. 25, pp. 8748-8753.
Heinen, A. et al., "p57$^{kip2}$'s role beyond schwann cell cycle control," *Cell Cycle*, Sep. 15, 2008, vol. 7, No. 18, pp. 2781-2786.
Honmou, S. et al., "Restoration of Normal Conduction Properties in Demyelinated Spinal Cord Axons in the Adult Rat by Transplantations of Exogenous Schwann Cells," *The Journal of Neuroscience*, May 15, 1996, vol. 16, No. 10, pp. 3199-3208.

(Continued)

*Primary Examiner* — John D Ulm
(74) *Attorney, Agent, or Firm* — Morgan, Lewis & Bockius LLP

(57) ABSTRACT

The present invention is based on the discovery of polyclonal IgG's ability to promote Schwann cell maturation, differentiation, and myelin production. Methods for treating non-idiopathic, demyelinating peripheral neuropathies in mammals, where the neuropathy is not immune-mediated or infection-mediated, through the administration of polyclonal IgG are provided. Types of demyelinating peripheral neuropathies treatable with the present invention include peripheral nerve trauma and toxin-induced peripheral neuropathies. Alternatively, a composition of polyclonal IgGs can be applied directly to a peripheral nerve cell to induce maturation, differentiation into a myelinating state, and myelin expression or promote cell survival.

64 Claims, 9 Drawing Sheets

(56) References Cited

OTHER PUBLICATIONS

Howard, M.A. et al., "Intracerebral drug delivery in rats with lesion-induced memory deficits," *J Neurosurg*, 1989, vol. 71, pp. 105-112.
International Search Report for International Patent Application No. PCT/US2013/028350 filed Feb. 28, 2013, 5 pages.
Krendel, D.A. et al., "Successful Treatment of Neuropathies in Patients With Diabetes Mellitus," *Arch Neurol*, Nov. 1995, vol. 52, pp. 1053-1061.
Kuhlmann, T. et al., "Differential Regulation of Myelin Phagocytosis by Macrophages/Microglia, Involvement of Target Myelin, Fc Receptors and Activation by Intravenous Immunoglobulins," *Journal of Neuroscience Research*, 2002, vol. 67, pp. 185-190.
Küry, P. et al., "Mammalian Achaete Scute Homolog 2 Is Expressed in the Adult Sciatic Nerve and Regulates the Expression of Krox24, Mob-1, CXCR4, and p57kip2 in Schwann Cells," *The Journal of Neuroscience*, Sep. 1, 2002, vol. 22, No. 17, pp. 7586-7595.
Langer, R. et al., "Chemical and Physical Structure of Polymers as Carriers for Controlled Release of Bioactive Agents: A Review," *JMS—Rev, Macromol. Chem. Phys.*, 1983, vol. C23, No. 1, pp. 61-126.
Langer, R., "New methods of drug delivery," *Science*, Sep. 28, 1990, vol. 249, pp. 1527-1533, Academic OneFile—Document, 12 pages.
Latov et al., "Immunological and infectious diseases of the peripheral nerves," May 28, 1998, p. 340.
Levy, R.J. et al., "Inhibition of Calcification of Bioprosthetic Heart Valves by Local Controlled-Release Diphosphonate," *Science*, Apr. 12, 1985, vol. 228, pp. 190-192.
Lin, H.H. et al., "Effective treatment of experimental autoimmune neuritis with human immunoglobulin," *Journal of the Neurological Sciences*, 2007, vol. 256, pp. 61-67.
MacDonald, D.R., "Neurological Complications of Chemotherapy," *Neurologic Complications of Systemic Cancer*, Nov. 1991, vol. 9, No. 4, pp. 955-967.
Nakahara, J. et al., "Expression of Fc receptor for immunoglobulin M in oligodendrocytes and myelin of mouse central nervous system," *Neuroscience Letters*, 2003, vol. 337, pp. 73-76.
Notghi, L.M. et al., "Neonatal axonal neuropathy: a curious presentation of congenital hypomyelination," *Clinical Neurophysiology*, Oct. 1, 2010, vol. 121, Abstract No. P12-12, 2 pages.
Odaka, M. et al., "Treatment Response to Steroid and Intravenous Immunoglobulin in a Patient with Chronic Sensory Demyelinating Neuropathy," *Journal of Clinical Neuromuscular Disease*, Jun. 2007, vol. 8, No. 4, pp. 207-211.
Rodrigues, M.C.O. et al., "Peripheral Nerve Repair with Cultured Schwann Cells: Getting Closer to the Clinics," *The Scientific World Journal*, Jan. 1, 2012, vol. 2012, pp. 1-10.
Saudek, C.D. et al., "A Preliminary Trial of the Programmable Implantable Medication System for Insulin Delivery," *The New England Journal of Medicine*, Aug. 31, 1989, vol. 321. No. 9, pp. 574-579.
Sefton, M.V., "Implantable Pumps," *CRC Critical Reviews in Biomedical Engineering*, 1987, vol. 14, No. 3, pp. 201-240.
Sekiguchi, K. et al., "Nerve conduction characteristics of infliximad induced demyelinating neuropathy," *Clinical Neurophysiology*, Oct. 1, 2010, vol. 121, Abstract No. P12-11, 1 page.
Stangel, M., "Transplantation myelinbildender Zellen als regenerative Therapie bei Multipler Sklerose," *Nervenarzt*, 2002, vol. 73, pp. 937-945.
Steiner, I. et al., "Neuropathies associated with herpes virus infection," *Immunology and Infectious Disease of the Peripheral Nerves*, Latov, N. eds., 1998, pp. 340-353.
Stübgen, J-P., "Drug-induced dysimmune demyelinating neuropathies," *Journal of the Neurological Sciences*, 2011, vol. 2307, pp. 1-8.
Vargas, M.E. et al., "Endogenous antibodies promote rapid myelin clearance and effective axon regeneration after nerve injury," *PNAS*, Jun. 29, 2010, vol. 107, No. 26, pp. 11993-11998.
Van Schaik, IN et al., "Immunomodulation and remyelination: two aspects of human polyclonal immunoglobulin treatment in immune mediated neuropathies?" *Multiple Sclerosis*, 1997, vol. 3, pp. 98-104.
Verma, A. et al., "High-dose intravenous immunoglobulin therapy in chronic progressive lumbosacral plexopathy," *Neurology*, 1994, vol. 44, No. 2, pp. 248-250.
Warrington, A.E. et al., "Human monoclonal antibodies reactive to oligodendrocytes promote remyelination in a model of multiple sclerosis," *PNAS*, Jun. 6, 2000, vol. 97, No. 12, pp. 6820-6825.
Warrington, A.E. et al., "A Recombinant Human IgM Promotes Myeline Repair After a Single, Very Low Dose," *Journal of Neuroscience Research*, 2007, vol. 85, pp. 967-976.
Zhang, J. et al., "A model for ex vivo spinal cord segment culture—A tool for analysis of injury repair strategies," *Journal of Neuroscience Methods*, 2010, vol. 192, pp. 49-57.
Zochodne, D.W. et al., "Failure of immunotherapy to prevent, arrest or reverse diabetic lumbosacral plexopathy," *Acta Neurologica Scandinavica*, 2003, vol. 107, pp. 299-301.
Fehlings, M.G, et al., "Immunoglobulin G: a potential treatment to attenuate neuroinflammation following spinal cord injury," *Journal of Clinical immunology*, 2010, vol. 30, pp. 109-112.
Gok, B. et al., "Immunomodulation of acute experimental spinal cord injury with human immunoglobulin G," *Journal of Clinical Neuroscience*, 2009, vol. 16, No. 4, pp. 549-533.
Wiles C.M. et al. Intravenous immunoglobulin in neurological disease: a specialist review. J Neurol Neurosurg Psychiatry, 2002, 72, pp. 440-448, c. 441, vol. 1.
Clinical Neurophysiology, 2010, vol. 121, p. S174, Poster No. P12-11.

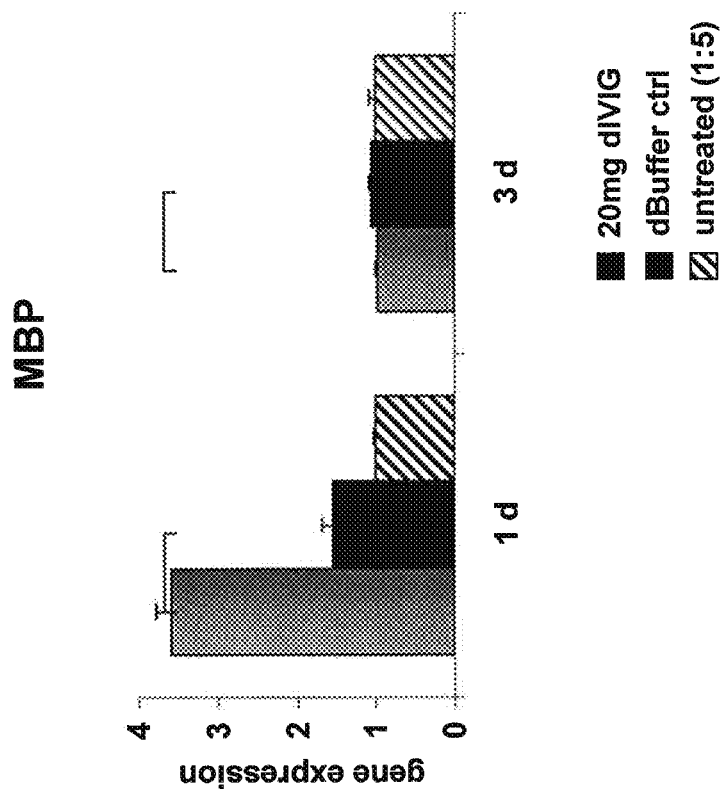
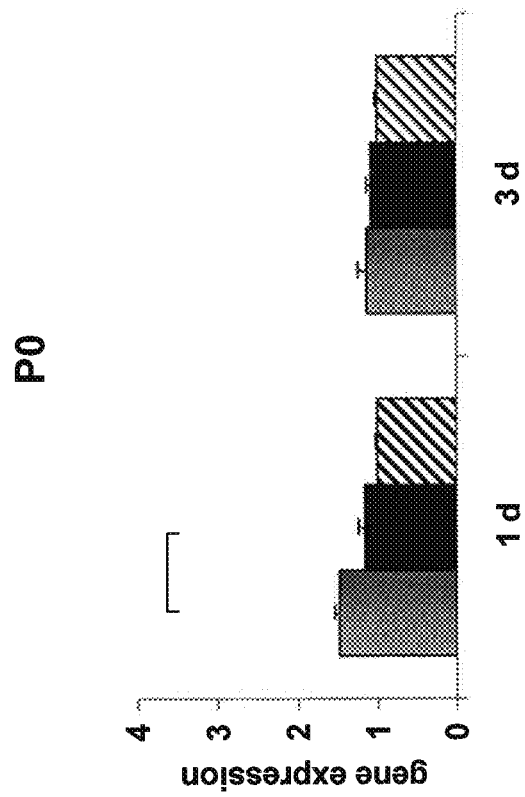

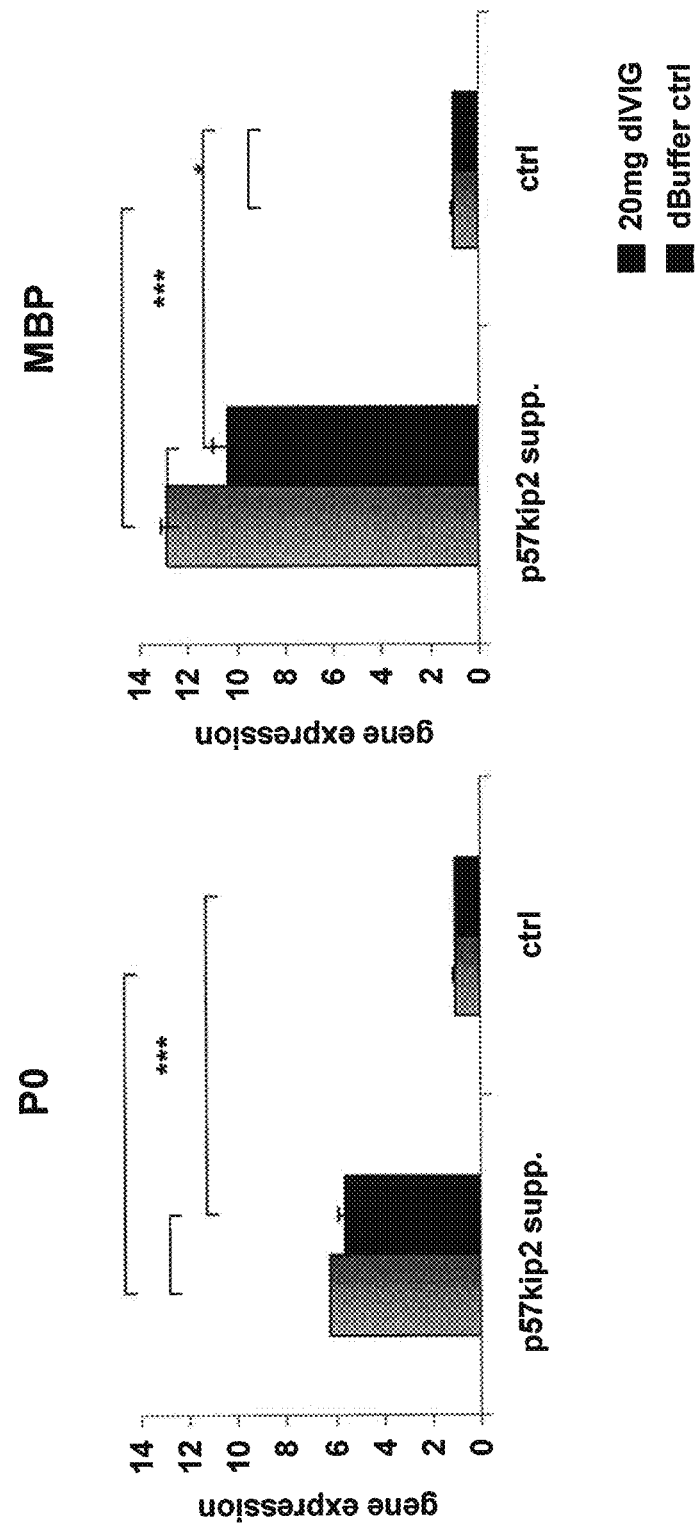

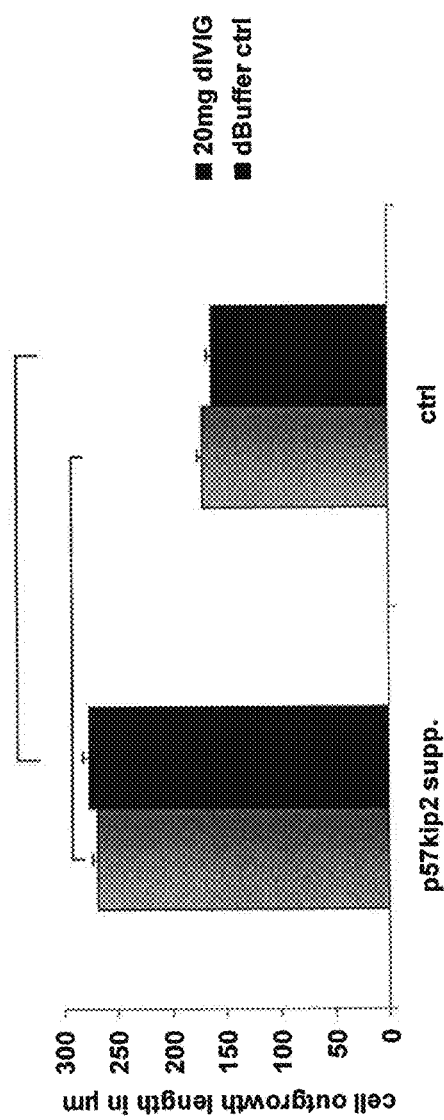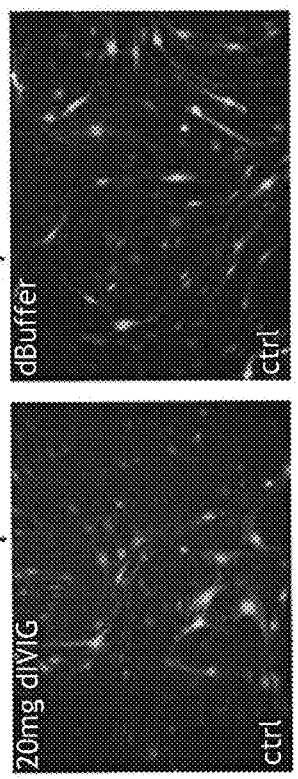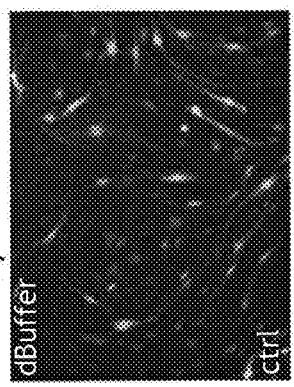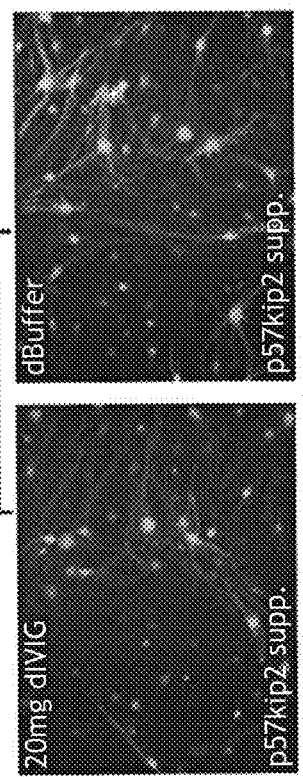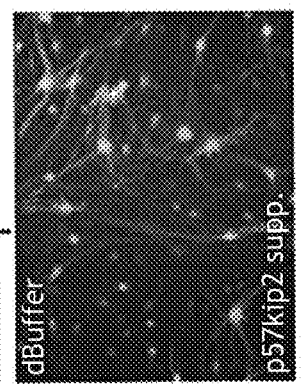

IGG STIMULATED REMYELINATION OF PERIPHERAL NERVES

CROSS REFERENCES TO APPLICATIONS

This application is a Continuation of U.S. patent application Ser. No. 14/625,542, filed Feb. 18, 2015, which is a Divisional of U.S. patent application Ser. No. 13/781,283 (issued as U.S. Pat. No. 8,986,670), filed Feb. 28, 2013, which claims priority to U.S. Provisional Patent Application Ser. No. 61/605,117 filed Feb. 29, 2012, the disclosures of which are hereby incorporated herein by reference in their entireties for all purposes.

BACKGROUND OF THE INVENTION

Peripheral neuropathy is a manifestation of disorders that inflict damage to the peripheral nervous system (PNS), a network of ganglia and neurons that transmit signals between the central nervous system (CNS), i.e. brain and spinal cord, and every other part of the body. Neurons of the PNS rely on Schwann cells for, e.g. myelination, accelerated nerve conduction, nerve development and regeneration, trophic support, production of nerve extracellular matrix, and modulation of neuromuscular synaptic activity. These Schwann cells provide electric insulation by wrapping a protein and lipid-rich myelin sheath around axons of motor and sensory neurons. Given myelin's critical role, it is not surprising that demyelination of peripheral axons is a hallmark of acute and chronic peripheral neuropathies such as Guillain-Barré syndrome (GBS), chronic demyelinating polyneuropathy (CIDP) and multifocal motor neuropathy (MMN) as well as other peripheral nerve pathologies induced by toxins, drugs or systemic diseases, e.g. diabetes.

Peripheral neuropathies can distort signal transmission, causing symptoms that vary with the origin of the neuropathy and type or number of nerves affected. For example, symptoms may depend on whether the disorder affects sensory nerve fibers, which transmit sensory information from the affected area to the CNS, or motor nerve fibers, which transmit impulses and coordinate motor activity from the CNS to a muscle, or both. Peripheral neuropathies can be classified as mononeuropathies, involving damage to one nerve, or polyneuropathies, involving damage of multiple nerves; acute, where symptoms appear suddenly, progress rapidly, and resolve slowly, or chronic, where symptoms begin subtly, and progress slowly. Over 100 different types of peripheral neuropathy have been identified to date. Clinical diagnoses of peripheral neuropathy can be made based on the clinical history of the subject, a physical examination, the use of electromyography (EMG) and nerve conduction studies (NCS), autonomic testing, and nerve biopsies, etc.

Current treatments for peripheral neuropathies are directed at the underlying condition, where possible, and often used in conjunction with symptomatic treatments, such as anti-inflammatory agents, pain management, mechanical aids, and/or surgical intervention, etc. The body also possesses its own regenerative capacity in response to injury or damage of the PNS. After injury to the PNS, Wallerian degeneration of distal nerve stumps occur, followed by Schwann cell degradation of myelin, phagocytosis of extracellular myelin, and recruitment of macrophages for further myelin clearance. Schwann cells can further adapt to pathological situations by its ability to dedifferentiate, proliferate, promote axonal regeneration and redifferentiate, and produce myelin. See Bhatheja et al. (2006) Int. J. Biochem. Cell Biol. 38(12):1995-9. In the course of repair, Schwann cells stimulate, guide axonal regeneration, and target reinnervation, forming a regeneration tube of the axon, known as Bunger's band, by proliferating rapidly and providing the axon with a path to grow along. See Burstyn-Cohen et al. (1998) J. Neurosci 18(21): 8875-8885. While functional nerve regeneration in the PNS can generally be observed (in contrast to CNS which lacks a regenerative mechanism for myelin clearance and axon regeneration), it is often limited or chronically impaired. Novel repair promoting approaches for the PNS are therefore needed.

Recent studies on the CNS have yielded evidence of IgM's direct effect on oligodendrocytes, the myelinating glial cells of the central nervous system. For instance, targeting of oligodendrocyte-reactive IgMκ antibodies to oligodendrocytes was found to promote CNS remyelination (Asakura et al., 1998). Other studies showed that treatment of a non-immune, toxin-induced model of demyelinating disease with pooled human IgM molecules results in a significantly enhanced oligodendrocyte differentiation in the CNS (Bieber et al., 2000; Bieber et al., 2002; Warrington et al., 2007). The discovery of Fc receptors for IgM on oligodendrocytes, their precursor cells, and myelin in the CNS, offers further clues of a possible ligand-receptor interaction (Nakahara et al., 2003).

Knowledge gained from these oligodendrocyte—IgM studies, though meaningful for CNS repair, fails to harness the regenerative capacity of the PNS (which contains no oligodendrocytes). In more relevant studies, administration of human IVIG was found to reduce disease duration in an EAN (autoimmune neuritis) rat model, simulating the PNS-specific, demyelinating Guillain-Barré syndrome (GBS) (Lin et al., 2007). The effects were postulated as being attributable to IVIG's immunomodulatory role and possible anti-inflammatory and secondary bystander axonal loss reduction capability. In a separate study of the humoral immune system, B-cell knockout RID mice exhibited significant delay in macrophage influx, myelin clearance, and axon regeneration after PNS injury. Rapid myelin debris clearance was restored through passive transfer of antibodies from naïve WT mice or anti-PNS myelin antibody, thereby confirming the role of endogenous antibodies in promoting macrophage entrance and phagocytic activity (Vargas et al., 2010). Clinical trials with administration of intravenous immunoglobulins (IVIG) have shown positive effects for GBS, chronic demyelinating polyneuropathy (CIDP) and multifocal motor neuropathy (MMN), with the assumption that treatment in each of these autoimmune or immune-mediated neuropathies was accomplished through IVIG's immunomodulatory role.

The effect of polyclonal IgG on Schwann cells, if any, was heretofore unknown. A question, therefore, remained as to how the regenerative function of Schwann cells could be harnessed for therapeutic purposes in demyelinating, peripheral neuropathies. The present discovery of exogenous polyclonal IgG's ability to induce Schwann cell maturation, differentiation, and myelin production, is an important clarification of mechanism that provides novel approaches to the treatment of all demyelinating peripheral neuropathies.

SUMMARY OF THE INVENTION

In one aspect of the invention, there is provided methods of treating a demyelinating peripheral neuropathy in mammals, wherein the neuropathy is not immune-mediated or infection-mediated, by administering a therapeutically effective amount of polyclonal IgG to a mammal diagnosed with said neuropathy. In some embodiments of the invention, the demyelinating peripheral neuropathy being treated is not Guillain-Barré syndrome, chronic demyelinating polyneuropathy, or multifocal motor neuropathy. In other embodiments of the invention, the demyelinating peripheral neuropathy is a non-idiopathic neuropathy. The demyelinating peripheral neuropathy treatable by the present invention may be selected from a trauma-induced neuropathy, a toxin-induced neuropathy, an inherited neuropathy, and a neuropathy induced by a metabolic disease, e.g. diabetic neuropathy.

In another aspect of the invention, there is provided methods of treating peripheral nerve trauma by administering a therapeutically effective amount of polyclonal IgG to a mammal with peripheral nerve trauma.

In yet another aspect of the invention, there is provided methods of treating toxin-induced peripheral neuropathy, wherein the neuropathy is not infection-mediated, by administering a therapeutically effective amount of polyclonal IgG to a mammal diagnosed with said neuropathy.

For treatment of a demyelinating peripheral neuropathy described herein, polyclonal IgG of the invention may be administered locally or systemically. Local administration of the polyclonal IgG can occur intramuscularly or intradermally. Systemic administration of the polyclonal IgG can occur intranasally, subcutaneously, orally, intra-arterially or intravenously. In some embodiments of the invention, an anti-inflammatory agent is co-administered with the polyclonal IgG to the mammal. The anti-inflammatory agent may be selected from an adrenocorticotropic hormone, a corticosteroid, an interferon, glatiramer acetate, or a non-steroidal anti-inflammatory drug.

The polyclonal IgG of the invention may be administered weekly, biweekly, or monthly at a dose of about 0.05 to 5 g per kg of patient body weight or about 0.5 to 2 g per kg of patient body weight.

In a further aspect of the invention, there is provided methods of promoting myelination of a peripheral nerve cell by a Schwann cell by contacting the Schwann cell with an amount of polyclonal IgG sufficient to promote myelination of said peripheral nerve cell by the Schwann cell.

In another aspect of the invention, there is provided methods of promoting the differentiation of an immature Schwann cell into a myelinating state by contacting said Schwann cell with polyclonal IgG in an amount sufficient to induce the Schwann cell differentiation.

In yet another aspect, there is provided methods of promoting myelin production by a Schwann cell comprising contacting said Schwann cell with an amount of polyclonal IgG sufficient to upregulate MBP gene.

In a further aspect of the invention, there is provided methods of culturing mammalian nervous tissue which comprises axons by contacting the tissue in culture with an effective amount of Schwann cells and an effective amount of polyclonal IgG, whereby the contacting of Schwann cells with polyclonal IgG induces upregulation of MBP gene.

In yet another aspect of the invention, there is provided methods of treating a peripheral nerve injury in a mammal by: transplanting nerve cells to a site of the peripheral nerve injury; and contacting the nerve cells with a composition comprising Schwann cells and polyclonal IgG.

In the methods described herein, the polyclonal IgG can be given through one or more routes of administration, such as intramuscularly, intradermally, subcutaneously, buccally, orally, intranasally, or intra-arterially or intravenously to an individual in need of such therapy. The individual may be a human or domesticated animal. In some embodiments, the polyclonal IgG is derived from pooled human serum.

In some embodiments, the polyclonal IgG Is co-administered with an anti-inflammatory agent to mammal in need of such therapy. The anti-inflammatory agent may be selected from an adrenocorticotropic hormone, a corticosteroid, an interferon, glatiramer acetate, or a non-steroidal anti-inflammatory drug.

In yet another aspect of the invention, there is provided pharmaceutical compositions comprising a pharmaceutically acceptable carrier and an effective amount of polyclonal IgG for treating a non-idiopathic, demyelinating peripheral neuropathy.

BRIEF DESCRIPTION OF THE DRAWINGS

More particular descriptions of the invention are made by reference to certain exemplary embodiments thereof which are illustrated in the appended Figures. These Figures form a part of the specification. It is to be noted, however, that the appended Figures illustrate exemplary embodiments of the invention and therefore are not to be considered limiting in their scope.

FIG. 2A and FIG. 1B show the relative proliferative rates of immature Schwann cells that were exposed to nondialysed (FIG. 2A) and dialysed (FIG. 2B) IVIG/buffer formulations after 2 days as measured using Ki-67 assays. These relative proliferation rates were generated based on the number of cells positive for Ki-67 expression during cell proliferation.

FIG. 3A and FIG. 3B show the levels of P0 (FIG. 3A) and MBP (FIG. 3B) gene expression in immature Schwann cells that were exposed to dialysed IVIG/buffer formulations at 1 day and 3 day time-points.

FIG. 4A and FIG. 4B show the levels of P0 (FIG. 4A) and MBP (FIG. 4B) gene expression in p57kip2 suppressed Schwann cells that were exposed to dialysed IVIG/buffer formulations at the 7 day time-point (9 days suppression).

FIG. 8A, FIG. 8B, FIG. 8C and FIG. 8D show a graph of the cell outgrowth length for p57kip2 suppressed Schwann cells and control transfected cells (FIG. 8A) after 7 days of stimulation with dialysed IVIG/buffer formulations (9 days suppression) along with the respective fluorescent images of the p57kip2 suppressed Schwann cells stimulated with 20 mg of IVIG (FIG. 8B), p57kip2 suppressed Schwann cells stimulated with buffer (FIG. 8C), control transfected cells treated with 20 mg IVIG (FIG. 8D), and control transfected cells treated with buffer (FIG. 8E).

DETAILED DESCRIPTION OF THE INVENTION

Figure 1B:
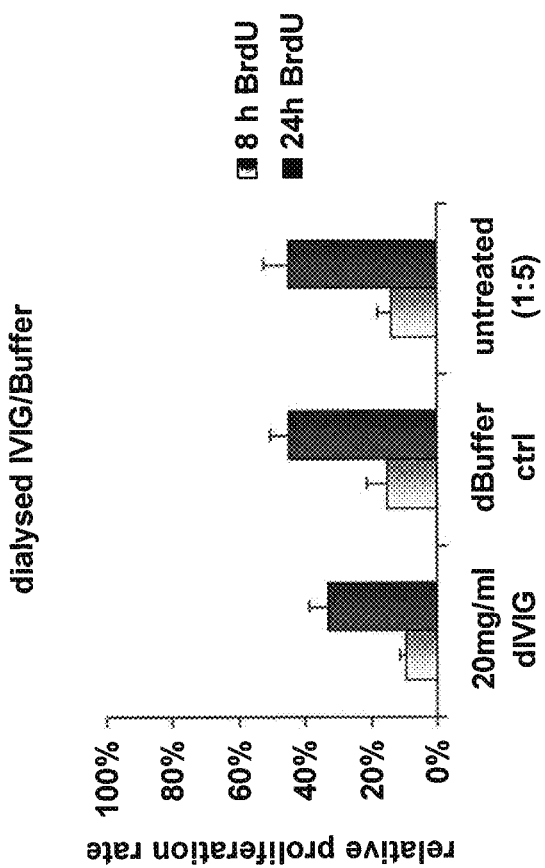
FIG. 1A and FIG. 1B show the relative proliferation rates of immature Schwann cells that were exposed to nondialysed (FIG. 1A) and dialysed (FIG. 1B) IVIG/buffer formulations after 2 days as measured by BrdU incorporation assays. These relative proliferation rates were generated based on the number of cells positive for of 5-bromo-2'-deoxyuridine (BrdU) incorporated into cellular DNA during cell proliferation.

The discovery of polyclonal IgG's ability to promote Schwann cell homeostasis, maturation, differentiation, and myelin production can be applied for treatment of demyelinating peripheral neuropathies of varying origins, e.g. toxin-induced neuropathies, diabetic neuropathy, trauma-induced neuropathy, by promoting the regenerative capacity of native Schwann cells. Contemplated is the administration of polyclonal IgG as an adjunct or replacement of existing therapeutic regimes or symptomatic treatments for demyelinating peripheral neuropathies. Furthermore, the present invention can be used in the laboratory setting for effecting peripheral nerve remyelination. Based on the findings described herein, polyclonal IgGs can be applied in nerve transplant, cell culture, e.g. induction of Schwann cell differentiation, determination of precursor cell fate, myelin gene regulation or protein expression, and as a pretreatment to or post-operative care regimen for surgical techniques threatening or involving peripheral nerves.

I. Definitions

The term "non-idiopathic" refers to a disorder where the underlying cause is known.

The term "peripheral neuropathy," as used herein, refers to a disorder affecting the peripheral nervous system, which excludes ganglion and nerves of the brain and the spinal cord. "Peripheral neuropathy" can manifest as one or a combination of motor, sensory, sensorimotor, or autonomic neural dysfunction. The variety of morphologies exhibited by peripheral neuropathies can be attributed to a number of different causes. For example, peripheral neuropathies can be genetically acquired, can result from a systemic disease, or can be induced by a toxic agent. Examples include but are not limited to diabetic peripheral neuropathy, distal sensorimotor neuropathy, or autonomic neuropathies such as reduced motility of the gastrointestinal tract or atony of the urinary bladder. Examples of peripheral neuropathies associated with systemic disease include post-polio syndrome or AIDS-associated neuropathy; examples of hereditary peripheral neuropathies include Charcot-Marie-Tooth disease, Abetalipoproteinemia, Tangier disease, Metachromatic leukodystrophy, Fabry's disease, and Dejerine-Sottas syndrome; and examples of peripheral neuropathies caused by a toxic agent include those caused by treatment with a chemotherapeutic agent such as vincristine, cisplatin, methotrexate, or 3'-azido-3'-deoxythymidine.

One variety of peripheral neuropathy is "demyelinating peripheral neuropathy." As used herein, a "demyelinating peripheral neuropathy" describes a broad class of peripheral neuropathies that are associated with the destruction or removal of myelin, the lipid-rich sheath surrounding and insulating nerve fibers, from nerves. Non-limiting examples of demyelinating peripheral neuropathy diseases include diabetic peripheral neuropathy, distal sensorimotor neuropathy, or autonomic neuropathies such as reduced motility of the gastrointestinal tract or atony of the urinary bladder. Further examples and descriptions of demyelinating peripheral neuropathy can be found in Section II of the Detailed Description.

An "immune-mediated" disorder, as used herein, refers to a condition which results from abnormal activity of the body's immune system. Subsets of "immune-mediated" disorder include, without limitation, autoimmune disease, wherein the immune system attacks the body, immune-complex disorders, disorders involving post-transplant rejection, inflammatory disease, and allergies.

An "infection-mediated" peripheral neuropathy refers to a dysfunction of the peripheral nervous system sustained as a result of viral, bacterial, or fungal infections.

A "trauma-induced peripheral neuropathy" or "traumatic peripheral neuropathy" refers to dysfunction of the peripheral nervous system caused by bodily shock, injury, or "physical trauma." Physical trauma, e.g. from combat, vehicular accidents, falls, and sports-related activities, can cause nerves to be partially or completely severed, crushed, compressed, or stretched, sometimes so forcefully that they are partially or completely detached from ganglia or the spinal cord and result in demyelination. Traum-induced peripheral neuropathies can also be sustained as a result of, e.g. electric shock, hypothermia, etc.

A "toxin" or "chemical induced" peripheral neuropathy refers to dysfunction of the peripheral nervous system caused by toxins (e.g., chemical agents). Toxins that produce peripheral neuropathy can generally be divided into three groups: drugs and medications; industrial chemicals; and environmental toxins. Non-limiting examples of toxins that can cause peripheral neuropathy are described below in Section II of the Detailed Description.

An "anti-inflammatory agent" as used herein includes any agent that reduces inflammation of an affected blood vessel and/or adjacent tissue. Non-limiting examples of anti-inflammatory agents are steroids (e.g., glucocorticoids and corticosteroids), immune selective anti-inflammatory derivatives (ImSAIDs), cooling agents, herbal supplements (e.g., devil's claw, hyssop, ginger, turmeric, arnica Montana, and willow bark (containing alicylilc acid), and foods with anti-inflammatory effects (e.g., pomegranate, green tea, vegetables, foods that contain omega-3 fatty acids), nuts, seeds, and extra-virgin olive oil). Specifically, prostaglandin 2 (PGE2) is a pro-inflammatory compound and PGE1 and PGE3 are anti-inflammatory compounds. Accordingly, agents that decrease PGE2 or increase PGE1 and PGE3 can also act as anti-inflammatory agents. Additional non-limiting examples of anti-inflammatory agents can be found in Section VI, "Combination Therapy," below.

An "immature Schwann cell," as used herein, refers to a specific stage in the Schwann cell lineage. The first step along the Schwann cell lineage gives the Schwann cell precursor, a proliferative cell that becomes associated with many axons and expresses the nerve growth factor receptor (NGF-R), growth-associated protein 43 (GAP-32), and the neural cell adhesion molecules N-CAM and L1. The subsequent "committed" Schwann cell is known as an immature Schwann cell; it becomes associated with progressively fewer axons and expresses, in addition to the previously noted markers, S-100 protein (from this stage onward, all Schwann cells express S-100). Committed Schwann cells develop into either nonmyelinating Schwann cells, which remain associated with several axons and express galactocerebroside (GalC) in addition to the previous markers, or into myelinating Schwann cells. Myelinating Schwann cells progress through a proliferative "premyelinating" stage, characterized by transient expression of suppressed cAMP-inducible Pou-domain transcription factor (SCIP), followed by a "promyelinating" GalC-positive stage, becoming associated with a single axon in the progress. The final differentiation into a mature myelinating Schwann cell involves downregulation of NGF-R, GAP-43, N-CAM, and L1 expression, with upregulation of expression of GalC and myelin proteins, and in vivo, the synthesis and elaboration of myelin.

The term "IgG," as used herein, refers to a composition of IgG immunoglobulins. The IgG class of immunoglobulins, as the name suggests, is characterized by the presence of a γ (gamma) heavy chain. An exemplary whole IgG immunoglobulin structure comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "immunoglobulin" or "antibody" is a polypeptide that is immunologically reactive with a particular antigen. The term "immunoglobulin," as used herein, encompasses intact molecules of various isotypes as well as fragments with antigen-binding capability, e.g., Fab', F(ab')2, Fab, Fv and rIgG. See, e.g., Pierce Catalog and Handbook, 1994-1995 (Pierce Chemical Co., Rockford, Ill.); Kuby, J., Immunology, 3.sup.rd Ed., W.H. Freeman & Co., New York (1998). The term also encompasses recombinant single chain Fv fragments (scFv). The term further encompasses bivalent or bispecific molecules, diabodies, triabodies, and tetrabodies. Bivalent and bispecific molecules are described in, e.g., Kostelny et al. (1992) J. Immunol. 148:1547, Pack and Pluckthun (1992) Biochemistry 31:1579, Hollinger et al., 1993, supra, Gruber et al. (1994) J. Immunol.: 5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

The term "polyclonal IgG," as used herein, refers to a heterogeneous collection of IgG immunoglobulins derived from multiple B-cells and having different specificities and epitope affinities. Methods of preparing polyclonal antibodies are known to the skilled artisan (e.g., Harlow & Lane, 1988, Antibodies: A Laboratory Manual. (Cold Spring Harbor Press)). The polyclonal IgGs of the invention can be extracted from plasma pooled from different mammalian individuals who have been prescreened for pathogenic disorders. In some embodiments, the polyclonal IgGs of the present invention are representative of over 100 individuals, over 200 individuals, over 300 individuals, over 400 individuals, over 500 individuals, over 600 individuals, over 700 individuals, over 800 individuals, over 900 individuals, over 1000 individuals, over 1100 individuals, over 1200 individuals, over 1300 individuals, over 1400 individuals, over 1500 individuals, over 1600 individuals, over 1700 individuals, over 1800 individuals, over 1900 individuals, or over 2000 individuals.

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. A ligand (e.g., an antibody) that specifically binds to a protein generally has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Myelin basic protein" (MBP), as used herein, refers to the gene as well as the protein encoded thereby, which is a major protein component of myelin, comprising approximately 30% of the total protein content of the myelin sheath. MBP has been shown to be a major target autoantigen in MS, and T cells reactive with MBP play a key role in its pathogenesis (see, for example, Schwartz, R S, "Autoimmunity and Autoimmune Diseases" in Paul, Fundamental Immunology, 3rd Ed. Raven Press, New York, 1993, pp. 1033 1097; Brown and McFarlin 1981. Lab Invest 45, pp. 278 284; Lehmann et al. 1992. Nature 358, pp. 155 157; Martin et al. 1992. Ann Rev Immunol 10, pp. 153 187; Sprent 1994. Cell 76, pp. 315 322; Su and Sriram. 1991. J of Neuroimmunol 34, pp. 181 190; and Weimbs and Stoffel. 1992. Biochemistry 31, pp. 12289 12296).

The term "axon" refers to an elongated fiber of a nerve cell responsible for conducting signals in the body.

The terms "individual," "subject," and "patient," used interchangeably herein, refer to a mammal, including, but not limited to, murines, simians, humans, mammalian farm animals, mammalian sport animals, and mammalian pets. In preferred embodiments, the individual is a human.

The terms "dose" and "dosage" are used interchangeably herein. A dose refers to the amount of active ingredient given to an individual at each administration. The dose will vary depending on a number of factors, including frequency of administration; size and tolerance of the individual; severity of the condition; risk of side effects; and the route of administration. One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

A "therapeutically effective" amount or dose or "sufficient/effective" amount or dose, is a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "treatment" or "therapy" generally means obtaining a desired physiologic effect. The effect may be prophylactic in terms of completely or partially preventing a disease or condition or symptom thereof and/or may be therapeutic in terms of a partial or complete cure for an injury, disease or condition and/or amelioration of an adverse effect attributable to the injury, disease or condition and includes arresting the development or causing regression of a disease or condition. Treatment can also include prophylactic use to mitigate the effects of injury, should it occur. For example, in one aspect, the present invention includes pre-administration to mitigate damage prior to surgery involving the peripheral nervous system. Treatment can also refer to any delay in onset, amelioration of symptoms, improvement in patient survival, increase in survival time or rate, etc. The effect of treatment can be compared to an individual or pool of individuals not receiving the treatment.

A "control" is used herein, refers to a reference, usually a known reference, for comparison to an experimental group. One of skill in the art will understand which controls are valuable in a given situation and be able to analyze data based on comparisons to control values. Controls are also valuable for determining the significance of data. For example, if values for a given parameter vary widely in controls, variation in test samples will not be considered as significant.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

II. Demyelinating Peripheral Neuropathies

The present invention is based on the discovery that polyclonal IgG can harness Schwann cells' regenerative capacity through stimulation of Schwann cell maturation, differentiation, and myelin production. In this manner, the invention targets a unifying mechanism of demyelinating peripheral neuropathies so as to provide a broad-spectrum treatment for such disorders. For example, this invention targets demyelinating peripheral neuropathies caused by physical trauma, toxic agents, and diabetes.

Demyelinating disorders treatable by the polyclonal IgG composition described herein include, for example, peripheral neuropathies that are genetically acquired, result from a systemic disease, or induced by a toxin or by trauma.

Genetic demyelinating neuropathies (also known as hereditary neuropathies) are one of the most common inherited neurological diseases. Genetic demyelinating neuropathies are divided into four major subcategories: 1) motor and sensory neuropathy, 2) sensory neuropathy, 3) motor neuropathy, and 4) sensory and autonomic neuropathy. Specifically, the demyelinating hereditary neuropathies are often progressive neuropathies with markedly decreased nerve conduction and velocity and chronic segmental demyelination of the peripheral nerve. Gabreels-Festen et al., "Hereditary demyelinating motor and sensory neuropathy," Brain Pathol. 3(2):135-146 (1993). Examples of general classes of genetic deyelinating neuropathies include but are not limited to diabetic peripheral neuropathy, distal sensorimotor neuropathy, or autonomic neuropathies such as reduced motility of the gastrointestinal tract or atony of the urinary bladder. Examples of hereditary peripheral neuropathies include Charcot-Marie-Tooth disease, Abetalipoproteinemia, Tangier disease, Metachromatic leukodystrophy, Fabry's disease, and Dejerine-Sottas syndrome.

Systemic demyelinating peripheral neuropathies arise as side effects of a systemic illness. Non-limiting examples of peripheral neuropathies associated with systemic disease include post-polio syndrome and AIDS-associated neuropathy. Furthermore, the following non-limiting systemic diseases can have peripheral neuropathy symptoms: cancer, malnutrition, alcoholism, diabetes, AIDS, Lyme disease, Rheumatoid arthritis, chronic kidney failure, autoimmune disorders, hypothyroidism, and viral infections (e.g., hepatitis).

Toxin induced demyelinating peripheral neuropathies are caused by exposure to neurotoxic agents such as pharmaceutical agents, biological agents, and chemical exposure. Examples of toxins that cause peripheral neuropathies include, but are not limited to, chemotherapeutic agents (e.g., vincristine, paclitaxel, cisplatin, methotrexate, or 3'-azido-3'-deoxythymidine), lead, mercury, thallium, organic solvents, pesticides, carbon disulfide, arsenic, acrylamide, diphtheria toxin, alcohol, anti-HIV medications (e.g., didanosine and zalcitabine), anti-tuberculosis medications (e.g., isoniazid and ethamubtol), antimicrobial drugs (e.g., dapsone, metronidazole, chloroquine, and chloamphenicol), psychiatric medications (e.g., lithium), radiation, and medications such as amiodarone, aurothioglucose: phenytoin, thalidomide, colchicine, cimetidine, disulfiram, hydralazine, and high levels of vitamin B6. Additional toxic agents that may cause peripheral neuropathy are listed below.

Trauma induced demyelinating peripheral neuropathies, as described above, are caused by bodily shock, injury, or physical trauma.

Accordingly, causes of peripheral neuropathy range widely, e.g. from diabetic complications; trauma; toxins including, without limitation, drugs and medications, industrial chemicals, and environmental toxins; autoimmune response; nutritional deficiencies; to vascular and metabolic disorders. For example, demyelinating peripheral neuropathies may occur as a result of osteosclerotic myeloma, monoclonal protein-associated peripheral neuropathy, hereditary motor and sensory peripheral neuropathies types 1 and 3, and hereditary susceptibility to pressure palsies.

Similarly, symptoms of a demyelinating peripheral neuropathy also vary, e.g. with the type of nerves affected. For example, a human patient having a demyelinating disorder can have one or more symptoms of a demyelinating disorder such as, but not limited to, impaired vision, numbness, weakness in extremities, tremors or spasticity, heat intolerance, speech impairment, incontinence, dizziness, or impaired proprioception (e.g., balance, coordination, sense of limb position). A human (e.g., a human patient) with a family history of a demyelinating disorder (e.g., a genetic predisposition for a demyelinating disorder), or who exhibits mild or infrequent symptoms of a demyelinating disorder described above can be, for the purposes of the method, considered at risk of developing a demyelinating disorder.

Specifically, sensory nerve damage caused by a demyelinating peripheral neuropathy can cause a more complex range of symptoms because sensory nerves have a wider, more highly specialized range of functions. Larger sensory fibers enclosed in myelin (lipid-rich membrane folds that are spirally wrapped and insulate many nerves) register vibration, light touch, and position sense. Damage to large sensory fibers lessens the ability to feel vibrations and touch, resulting in a general sense of numbness, especially in the hands and feet. Many patients cannot recognize by touch alone the shapes of small objects or distinguish between different shapes. This damage to sensory fibers may contribute to the loss of reflexes (as can motor nerve damage). Loss of position sense often makes individuals unable to coordinate complex movements like walking or fastening buttons, or to maintain their balance when their eyes are shut. Neuropathic pain is difficult to control and can seriously affect emotional well-being and overall quality of life.

Smaller sensory fibers without myelin sheaths transmit pain and temperature sensations. Damage to these fibers can interfere with the ability to feel pain or changes in temperature. Individuals may fail to sense that they have been injured from a cut or that a wound is becoming infected. Others may not detect pains that warn of impending heart attack or other acute conditions. (Loss of pain sensation is a particularly serious problem for individuals with diabetes, contributing to the high rate of lower limb amputations among this population.) Pain receptors in the skin can also become oversensitized, so that severe pain is felt (allodynia) from stimuli that are normally painless.

Symptoms of autonomic nerve damage are diverse and depend upon which organs or glands are affected. Autonomic nerve dysfunction can become life threatening and may require emergency medical care in cases when breathing becomes impaired or when the heart begins beating irregularly. Common symptoms of autonomic nerve damage include an inability to sweat normally, which may lead to heat intolerance; a loss of bladder control, which may cause infection or incontinence; and an inability to control muscles that expand or contract blood vessels to maintain safe blood pressure levels. A loss of control over blood pressure can cause dizziness, lightheadedness, or even fainting when an individual moves suddenly from a seated to a standing position (a condition known as postural or orthostatic hypotension).

Gastrointestinal symptoms frequently accompany autonomic neuropathy. Nerves controlling intestinal muscle contractions often malfunction, leading to diarrhea, constipation, or incontinence. Individuals may also experience difficulty eating or swallowing if certain autonomic nerves are affected.

The polyclonal IgG composition of the invention may also be used to treat demyelinating peripheral neuropathy which developed as a complication of diabetes, i.e. Type I, Type II. Peripheral neuropathy is one of the major complications of diabetes. Both a decrease in nerve conduction velocity and increased resistance to conduction failure caused by ischemia are among the earliest changes detected in diabetic patients and animal models of the disease. Ultrastructural studies have demonstrated changes in both axons and Schwann Cells (SC) (e.g., decrease in axon caliber and segmental demyelination) as well as in the microvasculature, all of which appear to develop independently. Some studies concluded that the progressive loss of fibers in peripheral nerves observed in human diabetic neuropathy may be due, at least in part, to delayed nerve degeneration and impaired nerve regeneration. Metabolic and microvascular abnormalities, as well as a deficiency in neurotrophins, have been considered responsible for the pathogenesis of diabetic neuropathy. The vascular alterations in diabetes consists mainly of ischemia and endoneurial hypoxia. The mechanisms underlying these vascular abnormalities include degenerative changes in the sympathetic nerve endings of vasa nervorum, with the consequent impairment in neural control of nerve blood flow and reduced production of prostacyclin and nitric oxide in nerves.

Two distinct clinical manifestations of diabetic neuropathy are those represented by patients suffering from painful symmetrical polyneuropathy, and by patients with insensitive, painless feet. The painless neuropathy is the prevalent disorder and, according to several studies, is likely to reflect the degree of nerve degeneration. The painful syndrome, on the other hand, is associated with fewer morphological abnormalities. While it has also been proposed that the painful syndrome may reflect nerve regeneration, as opposed to degeneration, several reports suggest that nerve regeneration is impaired in diabetes. Analysis of several functional indices in peripheral sensory nerves of diabetic rodents also suggests depressed, rather than increased, function. For instance, experimental diabetes induces several nociceptive responses including early thermal hyperalgesia that with time turns into hypoalgesia, mechanical hyperalgesia, thermal and tactile allodynia, increased C fiber activity and reduced sensitivity to opioids. In this context, mechanical hyperalgesia may result from increased firing after sustained suprathreshold mechanical stimulation of C fibers.

While therapies with antioxidants, vasodilators and neurotrophins may reverse some functional and metabolic abnormalities in diabetic nerves, they only result in a partial amelioration of abnormal pain perception, suggesting that other pathways are at play. The present invention is able to promote Schwann cell's healing capacity towards treatment of diabetic neuropathy.

The polyclonal IgG composition of the invention may also be used to treat demyelinating peripheral neuropathy resulting from trauma. A "trauma-induced" neuropathy refers to damage to the nervous system from external physical injury. Injury or sudden trauma, e.g. from warfare, automobile accidents, falls, and sports-related activities, can cause nerves to be partially or completely severed, crushed, compressed, or stretched, sometimes so forcefully that they are partially or completely detached from the spinal cord and result in demyelination. Less dramatic traumas also can cause serious nerve damage.

The polyclonal IgG composition of the invention may also be used to treat peripheral neuropathy caused by a toxic agent. Toxins that produce peripheral neuropathy can generally be divided into three groups: drugs and medications; industrial chemicals; and environmental toxins. As used herein, the term "toxic agent" is defined as any substance that, through its chemical action, impairs the normal function of one or more components of the peripheral nervous system. The definition includes agents that are airborne, ingested as a contaminant of food or drugs, or taken deliberately as part of a therapeutic regime.

The list of toxic agents that may cause peripheral neuropathy includes, but is not limited to, 3'-azido-3'-deoxythymidine, acetazolamide, acrylamide, adriamycin, alcohol, allyl chloride, almitrine, amitriptyline, amiodarone, amphotericin, arsenic, aurothioglucose, carbamates, carbon disulfide, carbon monoxide, carboplatin, chloramphenicol, chloroquine, cholestyramine, cimetidine, cisplatin, cis-platinum, clioquinol, colestipol, colchicine, colistin, cycloserine, cytarabine, dapsone, dichlorophenoxyacetic acid, didanosine; dideoxycytidine, dideoxyinosine, dideoxythymidine, dimethylaminopropionitrile, disulfiram, docetaxel, doxorubicin, ethambutol, ethionamide, ethylene oxide, FK506 (tacrolimus), glutethimide, gold, hexacarbons, hexane, hormonal contraceptives, hexamethylolmelamine, hydralazine, hydroxychloroquine, imipramine, indomethacin, inorganic lead, inorganic mercury, isoniazid, lithium, methylmercury, metformin, methotrexate, methylbromide, methylhydrazine, metronidazole, misonidazole, methyl N-butyl ketone, nitrofurantoin, nitrogen mustard, nitrous oxide, organophosphates, ospolot, paclitaxel, penicillin, perhexiline, perhexiline maleate, phenytoin, platinum, polychlorinated biphenyls, primidone, procainamide, procarbazine, pyridoxine, simvastatin, sodium cyanate, streptomycin, sulphonamides, suramin, tamoxifen, thalidomide, thallium, toluene, triamterene, trimethyltin, triorthocresyl phosphate, L-tryptophan, vacor, vinca alkaloids, vincristine, vindesine, megadoses of vitamin A, megadoses of vitamin D, zalcitamine, zimeldine; industrial agents, especially solvents; heavy metals; and sniffing glue or other toxic compounds.

The polyclonal IgG composition of the invention may also be used to treat demyelinating peripheral neuropathy resulting from the administration of chemotoxins for cancer therapy. Among the chemotoxins known to cause peripheral neuropathy are vincristine, vinblastine, cisplatin, paclitaxel, procarbazine, dideoxyinosine, cytarabine, alpha interferon, and 5-fluorouracil (see Macdonald, Neurologic Clinics 9: 955-967 (1991)).

III. Diagnosis and Monitoring of Demyelinating Peripheral Neuropathies

Diagnosis of demyelinating peripheral neuropathy can be made by a physician or clinician using one or more methods known in the art. A neurological examination is typically required and involves taking a patient history (including the patient's symptoms, work environment, social habits, exposure to any toxins, history of alcoholism, risk of HIV or other infectious disease, and family history of neurological disease), performing tests that may identify the cause of the neuropathic disorder, and conducting tests to determine the extent, site, and type of nerve damage.

A general physical examination and related tests may reveal the presence of a systemic disease causing nerve damage. Blood tests can detect diabetes, vitamin deficiencies, liver or kidney dysfunction, other metabolic disorders, and signs of abnormal immune system activity. An examination of cerebrospinal fluid that surrounds the brain and spinal cord can reveal abnormal antibodies associated with neuropathy. More specialized tests may reveal other blood or cardiovascular diseases, connective tissue disorders, or malignancies. Tests of muscle strength, as well as evidence of cramps or fasciculations, indicate motor fiber involvement. Evaluation of a patient's ability to register vibration, light touch, body position, temperature, and pain reveals sensory nerve damage and may indicate whether small or large sensory nerve fibers are affected.

Based on the results of the neurological exam, physical exam, patient history, and any previous screening or testing, additional testing may be ordered to help determine the nature and extent of the neuropathy. Exemplary technologies for aiding in the diagnosis of peripheral neuropathies include: computed tomography scan, magnetic resonance imaging, electromyography, nerve conduction velocity, nerve biopsy, or skin biopsy. Apparatuses useful in the diagnosis of peripheral neuropathies include, without limitation, U.S. Pat. No. 7,854,703.

Computed tomography, or CT scan, is a noninvasive, painless process used to produce rapid, clear two-dimensional images of organs, bones, and tissues. X-rays are passed through the body at various angles and are detected by a computerized scanner. The data is processed and displayed as cross-sectional images, or "slices," of the internal structure of the body or organ. Neurological CT scans can detect bone and vascular irregularities, certain brain tumors and cysts, herniated disks, encephalitis, spinal stenosis (narrowing of the spinal canal), and other disorders.

Magnetic resonance imaging (MRI) can examine muscle quality and size, detect any fatty replacement of muscle tissue, and determine whether a nerve fiber has sustained compression damage. The MRI equipment creates a strong magnetic field around the body. Radio waves are then passed through the body to trigger a resonance signal that can be detected at different angles within the body. A computer processes this resonance into either a three-dimensional picture or a two-dimensional "slice" of the scanned area.

Electromyography (EMG) involves inserting a fine needle into a muscle to compare the amount of electrical activity present when muscles are at rest and when they contract. EMG tests can help differentiate between muscle and nerve disorders.

Nerve conduction velocity (NCV) tests can precisely measure the degree of damage in larger nerve fibers, revealing whether symptoms are being caused by degeneration of the myelin sheath or the axon. During this test, a probe electrically stimulates a nerve fiber, which responds by generating its own electrical impulse. An electrode placed further along the nerve's pathway measures the speed of impulse transmission along the axon. Slow transmission rates and impulse blockage tend to indicate damage to the myelin sheath, while a reduction in the strength of impulses is a sign of axonal degeneration.

Nerve biopsy involves removing and examining a sample of nerve tissue, most often from the lower leg. Although this test can provide valuable information about the degree of nerve damage, it is an invasive procedure that is difficult to perform and may itself cause neuropathic side effects.

Skin biopsy is a test in which doctors remove a thin skin sample and examine nerve fiber endings. Unlike NCV, it can reveal damage present in smaller fibers; in contrast to conventional nerve biopsy, skin biopsy is less invasive, has fewer side effects, and is easier to perform.

Methods of monitoring an individual for demyelination or remyelination are known in the art. Monitoring a subject (e.g., a human patient) for remyelination, as defined herein, means evaluating the subject for a change, e.g., an improvement in one or more parameters that are indicative of remyelination, e.g., one can monitor improvement in one or more symptoms of a demyelinating disorder. Such symptoms include any of the symptoms of a demyelinating disorder described herein. Remyelination can also be monitored by methods which include direct determination of the state of myelin in the subject, e.g., one can measure white matter mass using magnetic resonance imaging (MRI) or measure the thickness of myelin fibers using a magnetic resonance spectroscopy (MRS) brain scan.

In some embodiments, the evaluation is performed at least 1 hour, e.g., at least 2, 4, 6, 8, 12, 24, or 48 hours, or at least 1 day, 2 days, 3 days, 4 days, 5 days, 6 days, 7 days, 8 days, 9 days, 10 days, 11, days, 12 days, 13 days, 14 days, 15 days, 16 days, 17 days, 18 days, 19 days, or 20 days or more, or at least 1 week, 2 weeks, 3 weeks, 4 weeks, 5 weeks, 6 weeks, 7 weeks, 8 weeks, 9 weeks, 10 weeks, 12 weeks, 13 weeks, 14 weeks, 15 weeks, 16 weeks, 17 weeks, 18 weeks, 19 weeks, 20 weeks or more, or any combination thereof, after an administration, preferably the first administration, of the polyclonal IgG. The subject can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for demyelinating disorders described herein. For example, continued administration of the polyclonal IgG could be done with one or more additional therapeutic agents where necessary. In a preferred embodiment, if a preselected outcome of the evaluation is obtained, an additional step is taken, e.g., the subject is administered another treatment or another evaluation or test is performed. The level of remyelination can be used to make a determination on patient care, e.g., a selection or modification of a course of treatment or the decision of a third party to reimburse for the treatment.

In some embodiments, monitoring a subject (e.g., a human patient) for remyelination can also include monitoring for a reduction in the size or number of inflammatory lesions (i.e., scleroses) using, e.g., Magnetic Resonance Imaging (MRI) scans, Positron-Emission Tomography (PET) scans, Diffusion-Weighted Imaging (DW-I, or DW-MRI), Diffusion Tensor Imaging, Myelography, Magnetization Transfer. In some embodiments, monitoring a subject for remyelination can include the detection of, e.g., (i) abnormal proteins such as tiny fragments of myelin, (ii) elevated levels of or specific types of lymphocytes, and/or (iii) abnormal levels of immunoglobulin (IgG) molecules. In other embodiments, monitoring a subject for remyelination can include assessment of a change in the subject's neuropsychology (e.g., the status of various abilities such as memory, arithmetic, attention, judgment and reasoning). In some embodiments, the monitoring of a subject (e.g., a human patient) for remyelination can involve testing a patient's urine for a decrease in levels of myelin basic protein-like material (MBP-like material), which substance becomes elevated as axonal damage occurs during disease progression. In some embodiments, where the demyelinating disorder affects a subject's eyes or vision, the monitoring of a subject for remyelination can involve testing for improvements in, e.g., color blindness.

Provided herein are methods of evaluating a subject, to determine, e.g., if a subject is responding or not responding to a treatment for a demyelinating disorder, e.g., a therapy that increases remyelination in a subject such as administering a polyclonal IgG. The method includes providing a reference value (e.g., a pre-administration value) for the level or state of myelin in the subject, and optionally, administering to the subject a medicament that increases remyelination (e.g., a polyclonal IgG). In embodiments where a medicament is administered, the method also includes providing a post-administration value for the level or state of myelin in the subject (e.g., the level or state of myelin following administration of a remyelination therapy) and comparing the post-administration value with the reference value, thereby evaluating the subject, e.g., determining if the subject is responding or not responding to the therapy. The post-administration value (i.e., the value corresponding to the state or level of myelin in a subject following a remyelination therapy) can be determined, e.g., by any of the assessment methods described herein. The reference value (i.e., the state or level of myelin in a subject prior to treatment with a remyelination therapy) can also be determined, e.g., by any of the assessment methods described herein.

In some embodiments, a determination that a subject is responding indicates that a shorter duration of treatment can/should/will be/is administered to the subject (e.g., shorter than the treatment which is recommended for a subject who is not responding to a therapy, or a duration shorter than currently used with existing therapies for demyelinating disorders, and optionally, that indication is entered into a record.

In some embodiments, a determination that a subject is responding indicates that a shorter duration of treatment is counter-indicated for the subject (e.g., a duration shorter than currently used with existing treatments for demyelinating disorders, e.g., any of the treatments for demyelinating disorders described herein), and optionally, that indication is entered into a record.

In some embodiments, providing a comparison of the post-administration value with a reference value includes: providing a determination of a post-administration level of myelin in a subject at a first time point (e.g., wherein the first time point is 6, 7, 8, 9, 10, 11, 12, 13, 14 or more days (e.g., 3, 4, 5, 6, 8 or more weeks (e.g., 3, 4, 6, 12 or more months))) after the commencement of administration of the remyelination therapy (e.g., polyclonal IgG); providing a determination of a reference value of the state or level of myelin in the subject at a second time point that is prior to the first time point (e.g., wherein the second time point is prior to, or within about 1, 2, 3, 4, or 5 days of the commencement of, administration of a remyelination therapy (e.g., polyclonal IgG); and providing a comparison of the post administration level and reference value of a subject's myelin, wherein increased levels of myelin in a subject (e.g., the levels differ by no more than about 60%, about 50%, about 40%, about 30%, about 20%, about 10%, about 5%, about 2%, or about 1%) between the post-administration level and reference value indicates that the subject is responding.

In some embodiments, the determination of whether a patient is responding to a therapy is made by evaluating the subject for a change, an improvement, in one or more parameters that are indicative of remyelination, e.g., one can monitor improvement in one or more symptoms of a demyelinating disorder. Such symptoms include any of the symptoms of a demyelinating disorder described herein. Remyelination can also be monitored by methods which include direct determination of the state of myelin in the subject, e.g., one can measure white matter mass using magnetic resonance imaging (MRI), measure the thickness of myelin fibers using a magnetic resonance spectroscopy (MRS) brain scan, or any other direct measures described herein.

In another embodiment, the determination of whether a patient is responding to a therapy can also be evaluated by any other assessment or indicia described herein, including, but not limited to, monitoring a patient for a reduction in the size or number of inflammatory lesions (i.e., scleroses) present in the patient; monitoring a patient's endoneurial fluid for a reduction in the presence or amount of, e.g., (i) elevated levels of or specific types of lymphocytes, and/or (ii) abnormal levels of immunoglobulin (IgG) molecules; monitoring a patient for a positive change in neuropsychology (e.g., the status of various abilities such as memory, arithmetic, attention, judgment and reasoning); and/or monitoring a patient's urine for a decrease in levels of myelin basic protein-like material (MBP-like material).

In some embodiments, at least a 5% (e.g., at least 10%, at least 15%, at least 20%, at least 25%, at least 30%, at least 35%, at least 40%, at least 50%, at least 60%, at least 70%) improvement in one or more symptoms of a demyelinating disorder or other above-described indicia following a remyelination therapy (e.g., a therapy that induces remyelination in a subject, e.g., a therapy such as a polyclonal IgG) is sufficient to classify the patient as responding to a therapy.

IV. Preparation of Polyclonal IgG

Immunoglobulin preparations according to the present invention can be prepared from any suitable starting materials. For example, immunoglobulin preparations can be prepared from donor serum or monoclonal or recombinant immunoglobulins. In a typical example, blood is collected from healthy donors. Usually, the blood is collected from the same species of animal as the subject to which the immunoglobulin preparation will be administered (typically referred to as "homologous" immunoglobulins). The immunoglobulins are isolated from the blood and purified by one or more suitable procedures, such as, for example, Cohn fractionation, ultracentrifugation, electrophoretic preparation, ion exchange chromatography, affinity chromatography, immunoaffinity chromatography, polyethylene glycol fractionation, alcohol fractionation, nanofiltration, ultrafiltration/diafiltration or the like. (See, e.g., Cohn et al., J. Am. Chem. Soc. 68:459-75 (1946); Oncley et al., J. Am. Chem. Soc. 71:541-50 (1949); Barundern et al., Vox Sang. 7:157-74 (1962); Koblet et al., Vox Sang. 13:93-102 (1967); Teschner et al. Vox Sang (92):42-55 (2007); Hoppe et al. Munch Med Wochenschr (34): 1749-1752 (1967), Falksveden (Swedish Patent No. 348942); Tanaka et al., Braz J Med Biol Res (33)37-30 (2000); Lebing et al., Vox Sang (84):193-201 (2003); U.S. Pat. Nos. 5,122,373 and 5,177,194; PCT/US2010/036470; and PCT/US2011/038247; the disclosures of which are incorporated by reference herein.)

To inactivate various viral contaminants present in plasma-derived products, the clarified PptG filtrate may be subjected to a solvent detergent (S/D) treatment. Methods for the detergent treatment of plasma derived fractions are well known in the art (for review see, Pelletier J P et al., Best Pract Res Clin Haematol. 2006; 19(1):205-42). Generally, any standard S/D treatment may be used in conjunction with the methods provided herein.

To further purify and concentrate IgG, cation exchange and/or anion exchange chromatography can be employed. Methods for purifying and concentrating IgG using ion exchange chromatography are well known in the art. For example, U.S. Pat. No. 5,886,154 describes a method in which a Fraction II+III precipitate is extracted at low pH (between about 3.8 and 4.5), followed by precipitation of IgG using caprylic acid, and finally implementation of two anion exchange chromatography steps. U.S. Pat. No. 6,069,236 describes a chromatographic IgG purification scheme that does not rely on alcohol precipitation at all. PCT Publication No. WO 2005/073252 describes an IgG purification method involving the extraction of a Fraction II+III precipitate, caprylic acid treatment, PEG treatment, and a single anion exchange chromatography step. U.S. Pat. No. 7,186,410 describes an IgG purification method involving the extraction of a Fraction I+II+III or Fraction II precipitate followed by a single anion exchange step performed at an alkaline pH. U.S. Pat. No. 7,553,938 describes a method involving the extraction of a Fraction I+II+III or Fraction II+III precipitate, caprylate treatment, and either one or two anion exchange chromatography steps. U.S. Pat. No. 6,093,324 describes a purification method comprising the use of a macroporous anion exchange resin operated at a pH between about 6.0 and about 6.6. U.S. Pat. No. 6,835,379 describes a purification method that relies on cation exchange chromatography in the absence of alcohol fractionation. The disclosures of the above publications are hereby incorporated by reference in their entireties for all purposes To reduce the viral load of an IgG composition provided herein, the composition may be nanofiltered using a suitable nanofiltration device. In certain embodiments, the nanofiltration device will have a mean pore size of between about 15 nm and about 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of between about 15 nm and about 72 nm, or between about 19 nm and about 35 nm, or of about 15 nm, 19 nm, 35 nm, or 72 nm. In a preferred embodiment, the nanofilter will have a mean pore size of about 35 nm, such as an Asahi PLANOVA 35N filter or equivalent thereof. In a particular embodiment, the IgG composition recovered from the anion exchange step is nanofiltered using a nanofilter having a pore size between 30 nm and 40 nm, preferably 35±2 nm. In another preferred embodiment, the nanofilter will have a mean pore size of about 19 or 20 nm, such as an Asahi PLANOVA 20N filter (19±2 nm) or equivalent thereof. In a particular embodiment, the IgG composition recovered from the anion exchange step is nanofiltered using a nanofilter having a pore size between 15 nm and 25 nm, preferably 19±2 nm.

In certain embodiments, immunoglobulin is prepared from gamma globulin-containing products produced by the alcohol fractionation and/or ion exchange and affinity chromatography methods well known to those skilled in the art. Purified Cohn Fraction II is commonly used. The starting Cohn Fraction II paste is typically about 95 percent IgG and is comprised of the four IgG subtypes. The different subtypes are present in Fraction II in approximately the same ratio as they are found in the pooled human plasma from which they are obtained. The Fraction II is further purified before formulation into an administrable product. For example, the Fraction II paste can be dissolved in a cold purified aqueous alcohol solution and impurities removed via precipitation and filtration. Following the final filtration, the immunoglobulin suspension can be dialyzed or diafiltered (e.g., using ultrafiltration membranes having a nominal molecular weight limit of less than or equal to 100,000 daltons) to remove the alcohol. The solution can be concentrated or diluted to obtain the desired protein concentration and can be further purified by techniques well known to those skilled in the art.

Preparative steps can be used to enrich a particular isotype or subtype of immunoglobulin. For example, protein A, protein G or protein H sepharose chromatography can be used to enrich a mixture of immunoglobulins for IgG, or for specific IgG subtypes. (See generally Harlow and Lane, Using Antibodies, Cold Spring Harbor Laboratory Press (1999); Harlow and Lane, Antibodies, A Laboratory Manual, Cold Spring Harbor Laboratory Press (1988); U.S. Pat. No. 5,180,810.)

Commercial sources of polyclonal immunoglobulins can also be used. Such sources include but are not limited to: Kiovig® 10% IVIG (Baxter Healthcare); Gammagard Liquid® 10% IVIG (Baxter Healthcare); Gammagard S/D® (Baxter Healthcare); Gammagard S/D® with less than 1 mg/mL of IgA in a 5% solution (Baxter Healthcare); Gamunex®-C, 10% (Grifols USA); Flebogamma®, 5% and 10% DIF (Grifols USA); Privigen® 10% Solution (CSL Behring); Carimune® NF or Sandoglobulin® (CSL Behring); and Hizentra® 20% Liquid (CSL Behring); Octagam®, 5% and 10% IVIG (Octapharma AG); Gammanorm® 16.5% SCIG (Octapharma AG). The commercial source of immunoglobulin preparation for use in the methods of the present invention is not critical.

An alternative approach is to use fragments of antibodies with antigen-binding capability, e.g., Fab', F(ab')2, Fab, Fv and rIgG. See, e.g., Pierce Catalog and Handbook, 1994-1995 (Pierce Chemical Co., Rockford, Ill.); Kuby, J., Immunology, 3.sup.rd Ed., W.H. Freeman & Co., New York (1998). The polyclonal IgG composition of the invention may include fragments of one immunoglobulin isotype, i.e. IgG, or can contain a mixture of immunoglobulin fragments of different isotypes (e.g., IgA, IgD, IgE, IgG and/or IgM). The Fc preparation also can contain predominantly (at least 60%, at least 75%, at least 90%, at least 95%, or at least 99%) fragments from the IgG immunoglobulin isotype, and can contain minor amounts of the other subtypes. For example, an Fc preparation can contain at least at least about 75%, at least about 90%, at least about 95%, or at least about 99% IgG fragments. In addition, the polyclonal IgG preparation can comprise a single IgG subtype or a mixture of two or more of IgG subtypes. Suitable IgG subtypes include IgG1, IgG2, IgG3, and IgG4. In a specific embodiment, the polyclonal IgG preparation comprises IgG1 fragments.

Immunoglobulins can be cleaved at any suitable time during preparation to yield Fab, F(ab') and/or F(ab')2 fragments, as applicable. A suitable enzyme for cleavage is, for example, papain, pepsin or plasmin. (See, e.g., Harlow and Lane, Using Antibodies, Cold Spring Harbor Laboratory Press (1999); Plan and Makula, Vox Sanguinis 28:157-75 (1975).) After cleavage, the Fc portions can be separated from the Fab, F(ab') and/or F(ab')2 fragments by, for example, affinity chromatography, ion exchange chromatography, gel filtration, or the like. In a specific example, immunoglobulins are digested with papain to separate the Fc fragment from the Fab fragments. The digestion mixture is then subjected to cationic exchange chromatography to separate the Fc fragments from the Fab fragments.

Immunoglobulin fragments can also be prepared from hybridomas or other culture system which express monoclonal antibody. (See, e.g., Kohler and Milstein, Nature 256:495-97 (1975); Hagiwara and Yuasa, Hum. Antibodies Hybridomas 4:15-19 (1993); Kozbor et al., Immunology Today 4:72 (1983); Cole et al., in Monoclonal Antibodies and Cancer Therapy, Alan R. Liss, Inc., pp. 77-96 (1985).) Human monoclonal antibodies can be obtained, for example, from human hybridomas (see, e.g., Cote et al., Proc. Natl. Acad. Sci. USA 80:2026-30 (1983)) or by transforming human B cells with EBV virus in vitro (see, e.g., Cole et al., supra). Monoclonal antibodies produced from hybridomas can be purified and the Fc fragments separated from the Fab, F(ab') and/or F(ab')2 fragments as described herein or as known to the skilled artisan.

IgG fragments also can be produced recombinantly, such as from eukaryotic cell culture systems. For example, a single chain Fv fragments (scFv) can be recombinantly produced by Chinese hamster ovary (CHO) cells transfected with a vector containing a DNA sequence encoding the Fv fragments. Methods for creating such recombinant mammalian cells are described in, for example, Sambrook and Russell, Molecular Cloning, A Laboratory Manual, 3rd ed. (Cold Spring Harbor Laboratory Press (New York) 2001)

and Ausubel et al., Short Protocols in Molecular Biology, 4th ed. (John Wiley & Sons, Inc. (New York) 1999) and are known to the skilled artisan. Recombinant immunoglobulin fragments can also be produced in other mammalian cell lines, such as baby hamster kidney (BHK) cells. Methods of culturing recombinant cells to produce recombinant proteins are also known to the art.

A variety of other expression systems can be utilized to express recombinant immunoglobulins IgG fragments. These include, but are not limited to, insect cell systems and microorganisms such as yeast or bacteria which have been transfected or transformed with an expression cassette encoding the desired IgG fragment. In certain embodiments, the microorganism optionally can be engineered to reproduce glycosylation patterns of mammalian or human IgG fragments.

In certain embodiments, further preparative steps can be used in order to render an immunoglobulin preparation safe for use in the methods according to the present invention. Such steps can include, for example, treatment with solvent/detergent, pasteurization and sterilization. Additional preparative steps may be used in order to ensure the safety of a polyclonal IgG preparation. Such preparative steps can include, for example, enzymatic hydrolysis, chemical modification via reduction and alkylation, sulfonation, treatment with B-propiolactone, treatment at low pH, or the like. Descriptions of suitable methods can also be found in, for example, U.S. Pat. Nos. 4,608,254; 4,687,664; 4,640,834; 4,814,277; 5,864,016; 5,639,730 and 5,770,199; Romer et al., Vox Sang. 42:62-73 (1982); Romer et al., Vox Sang. 42:74-80 (1990); and Rutter, J. Neurosurg. Psychiat. 57 (Suppl.):2-5 (1994) (the disclosures of which are incorporated by reference herein).

V. Pharmaceutical Compositions and Dosages

An individual in whom administration of the polyclonal IgG as set forth herein is an effective therapeutic regimen for demyelinating peripheral neuropathy, is preferably a human, but can be any mammal. Thus, as can be readily appreciated by one of ordinary skill in the art, the methods and pharmaceutical compositions of the present invention are particularly suited to administration to any a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

It is contemplated that a pharmaceutical composition comprising polyclonal IgG of the present invention can be administered by a variety of methods known in the art. The route and/or mode of administration vary depending upon the desired results, but will typically be intravenous, intramuscular, intranasal, intraperitoneal, intra-arterial, or subcutaneous. The pharmaceutical composition can include an acceptable carrier suitable for intravenous, intramuscular, subcutaneous, parenteral, spinal or epidermal administration (e.g., by injection or infusion).

The polyclonal IgG of this invention are useful for local or systemic administration for prophylactic and/or therapeutic treatment. Exemplary modes of administration include, without limitation, transdermal, subcutaneous, intra-arterial, intravenous, intranasal, intramuscular, rectal, buccal, and oral administration. The pharmaceutical compositions can be administered in a variety of unit dosage forms depending upon the method of administration. For example, unit dosage forms include powder, tablets, pills, capsules, suppositories, ampoules, and lozenges. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian. The pharmaceutical polyclonal IgG immunoglobin compositions of this invention, when administered orally, are preferably protected from digestion. This is typically accomplished either by complexing the antibodies with a composition to render them resistant to acidic and enzymatic hydrolysis or by packaging the antibodies in an appropriately resistant carrier such as a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid). Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a composition of polyclonal IgG with a pharmaceutically acceptable carrier, preferably an aqueous carrier. A variety of aqueous carriers can be used, e.g., buffered saline and the like.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (g) adsorptive carriers, e.g., kaolin and bentonite; (i) lubricants, e.g., talc, calcium and magnesium stearate and solid polyethylene glycols. The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions of the invention are sterile and generally free of undesirable matter. For parental administration, solutions and suspensions should be sterile, e.g., water or arachis oil contained in ampoules and, if appropriate, blood-isotonic. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the polyclonal IgG in these formulations can vary widely, and will be selected primarily based on fluid volumes, viscosities, patient body weight and the like in accordance with the particular mode of administration selected and the patient's needs.

Proper fluidity of the composition can be maintained, for example, by use of coating such as lecithin, by maintenance of required particle size in the case of dispersion and by use of surfactants. In some cases, it is preferable to include isotonic agents, for example, sugars such as sucrose, polyalcohols such as mannitol or sorbitol, and sodium chloride in the composition. Stabilizers such as nicotinamide, L-proline, L-glycine, or L-isoleucine may also be employed. Long-term absorption of the injectable compositions can be brought about by including in the composition an agent which delays absorption, for example, aluminum monostearate or gelatin.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil), and sweetening agents, (e.g., saccharin and aspartame).

The pharmaceutical compositions will generally contain from 0.5 to 90% of the active ingredient by weight of the total composition.

In addition to the monoclonal antibodies, the pharmaceutical compositions and medicaments can also contain other pharmaceutically active compounds, e.g. steroids, anti-inflammatory agents or the like.

Any diluent in the medicaments of the present invention may be any of those mentioned above in relation to the pharmaceutical compositions. Such medicaments may include solvents of molecular weight less than 200 as the sole diluent.

Pharmaceutical compositions of the invention can be prepared in accordance with methods well known and routinely practiced in the art. See, e.g., Remington: *The Science and Practice of Pharmacy*, Mack Publishing Co., 20th ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the immunoglobulin preparation is employed in the pharmaceutical compositions of the invention. The pharmaceutical composition can be formulated into dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels can be varied so as to obtain an amount of the active ingredient which is effective to achieve the desired therapeutic response for a particular patient without being toxic to the patient. A physician can start doses of the pharmaceutical composition at levels lower than that required to achieve the desired therapeutic effect and gradually increase the dosage until the desired effect is achieved. In general, effective doses vary depending upon many different factors, including the specific disease or condition to be treated, its severity, physiological state of the patient, other medications administered, and whether treatment is prophylactic or therapeutic.

The polyclonal IgG composition can be administered on multiple occasions. Intervals between single dosages can be daily, weekly, biweekly, every 3 weeks, every 4 weeks, monthly or yearly. Intervals can also be irregular as indicated by measuring therapeutic progress in the patient. Dosage and frequency can vary depending on the half-life of the antibodies in the patient.

Alternatively, the polyclonal IgG can be delivered in a controlled release system. For example, the polyclonal immunoglobulins may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., a site of injury in the peripheral nervous system, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In the case of a polyclonal IgG immunoglobulin preparation, intravenous immunoglobulin (IVIG) is commonly used. IVIG formulations are designed for administration by injection. Because polyclonal IgG preparations have achieved an exceptionally high immunoglobulin concentration (e.g. 10% w/v in some embodiments, 15% w/v in other embodiments, 20% w/v in still other embodiments, and up to 25% w/v in still further embodiments), which significantly reduces the volume for a therapeutically effective dose, the composition of the present invention is particularly advantageous for subcutaneous and/or intramuscular administration to a patient, as well as intravenous administration.

The term "effective amount" refers to an amount of polyclonal IgG preparation that results in an improvement or remediation of a medical condition being treated in the subject (e.g., for treating peripheral nerve trauma, for treating toxin-induced peripheral neuropathy, etc.). An effective amount to be administered to the subject can be determined by a physician with consideration of individual differences in age, weight, disease severity, route of administration (e.g., intravenous v. subcutaneous) and response to the therapy.

The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual.

A suitable dose of polyclonal IgG may be administered to a patient weekly, biweekly, every 3 weeks, every 4 weeks, or monthly to a subject, wherein the dose ranges from about 0.050 to 5 g/kilogram of patient body weight, about 0.095 to 4.7 g/kilogram of patient body weight, about 0.140 to 4.4 g/kilogram of patient body weight, about 0.185 to 4.1 g/kilogram of patient body weight, about 0.230 to 3.8 g/kilogram of patient body weight, about 0.275 to 3.5 g/kilogram of patient body weight, about 0.320 to 3.2 g/kilogram of patient body weight, about 0.365 to 2.9 g/kilogram of patient body weight, about 0.410 to 2.6 g/kilogram of patient body weight, about 0.455 to 2.3 g/kilogram of patient body weight, about 0.500 to 2.0 g/kilogram of patient body weight.

In alternative embodiments, the polyclonal IgG composition of the invention is administered weekly, biweekly, every 3 weeks, every 4 weeks, or monthly to a subject at a dose of about 0.05 to 4.9 g/kilogram of patient body weight, about 0.05 to 4.8 g/kilogram of patient body weight, about 0.05 to 4.7 g/kilogram of patient body weight, about 0.05 to 4.6 g/kilogram of patient body weight, about 0.05 to 4.5 g/kilogram of patient body weight, about 0.05 to 4.4 g/kilogram of patient body weight, about 0.05 to 4.3 g/kilogram of patient body weight, about 0.05 to 4.2 g/kilogram of patient body weight, about 0.05 to 4.1 g/kilogram of patient body weight, about 0.05 to 4.0 g/kilogram of patient body weight, about 0.05 to 3.9 g/kilogram of patient body weight, about 0.05 to 3.8 g/kilogram of patient body weight, about 0.05 to 3.7 g/kilogram of patient body weight, about 0.05 to 3.6 g/kilogram of patient body weight, about 0.05 to 3.5 g/kilogram of patient body weight, about 0.05 to 3.4 g/kilogram of patient body weight, about 0.05 to 3.3 g/kilogram of patient body weight, about 0.05 to 3.2 g/kilogram of patient body weight, about 0.05 to 3.1 g/kilogram of patient body weight, about 0.05 to 3.0 g/kilogram of patient body weight, about 0.05 to 2.9 g/kilogram of patient body weight, about 0.05 to 2.8 g/kilogram of patient body weight, about 0.05 to 2.7 g/kilogram of patient body weight, about 0.05 to 2.6 g/kilogram of patient body weight, about 0.05 to 2.5 g/kilogram of patient body weight, about 0.05 to 2.4 g/kilogram of patient body weight, about 0.05 to 2.3 g/kilogram of patient body weight, about 0.05 to 2.2 g/kilogram of patient body weight, about 0.05 to 2.1 g/kilogram of patient body weight, about 0.05 to 2.0 g/kilogram of patient body weight, about 0.05 to 1.9 g/kilogram of patient body weight, about 0.05 to 1.8 g/kilogram of patient body weight, about 0.05 to 1.7 g/kilogram of patient body weight, about 0.05 to 1.6 g/kilogram of patient body weight, about 0.05 to 1.5 g/kilogram of patient body weight, about 0.05 to 1.4 g/kilogram of patient body weight, about 0.05 to 1.3 g/kilogram of patient body weight, about 0.05 to 1.2 g/kilogram of patient body weight, about 0.05 to 1.1 g/kilogram of patient body weight, about 0.05 to 1.0 g/kilogram of patient body weight. Clinicians familiar with the diseases treated by IgG preparations can determine the appropriate dose for a patient according to criteria known in the art.

In other embodiments, an IVIG product can be administered to a subject within the range of about 0.2 g/kilogram of patient body weight to about 4 g/kilogram patient body weight each time, and the frequency of administration may range from twice a week, once a week, twice a month, once a month, or once every other month. One exemplary dose range of IVIG is between about 0.1 to about 1 or about 0.2 to about 0.8 g/kg patient body weight, typically administered at the frequency of twice a month or once a month. For instance, IVIG is administered to some patients at the dose of 0.2, 0.4, 0.6, or 0.8 g/kg patient body weight according to a twice-a-month schedule. In other cases, IVIG is administered at the dose of 0.2, 0.4, 0.6 or 0.8 g/kg patient body weight according to a once-a-month schedule.

The duration of IVIG treatment for a demyelinating peripheral neuropathy can vary: it may be as short as 3 or 6 months, or may be as long as 18 months, 2 years, 5 years, or 10 years. In some cases, the IVIG treatment may last the remainder of a patient's natural life. Effectiveness of the IVIG treatment may be assessed during the entire course of administration after a certain time period, e.g., every 3 months or every 6 months for an 18-month treatment plan. In other cases, effectiveness may be assessed every 9 or 12 months for a longer treatment course. The administration schedule (dose and frequency) may be adjusted accordingly for any subsequent administration.

For intravenous administration, the polyclonal IgG is administered at an exemplary initial infusion rate of 0.5 mL/kg/hr (0.8 mg/kg/min) for 30 minutes whereas the exemplary maintenance infusion rate would be to increase the rate every 30 minutes if tolerated up to 5 mL/kg/hr (8 mg/kg/min). Infusion times may vary depending on the dose, rate of infusion and tolerability.

For subcutaneous administration to individuals of 40 kg patient body weight and greater, an exemplary initial infusion rate is 30 mL/site at 20 mL/hr/site whereas an exemplary maintenance infusion rate is 30 mL/site at 20-30 mL/hr/site. For subcutaneous administration to individuals of less than 40 kg patient body weight, an exemplary initial infusion rate is 20-30 mL/site at 15 mL/hr/site whereas an exemplary maintenance infusion rate is 20 mL/site at 15-20 mL/hr/site. Infusion times may vary depending on the dose, rate of infusion and tolerability.

In accordance with the present invention, the time needed to complete a course of the treatment can be determined by a physician and may range from as short as one day to more than a month. In certain embodiments, a course of treatment can be from 1 to 6 months.

Methods for preparing parenterally administrable compositions will be known or apparent to those skilled in the art and are described in more detail in such publications as Remington's Pharmaceutical Science, 15th ed., Mack Publishing Company, Easton, Pa. (1980).

VI. Combination Therapy

In some embodiments, the polyclonal IgG can be administered to a subject as a combination therapy with another treatment, e.g., another treatment for a demyelinating disorder (e.g., any of the demyelinating disorders described herein. For example, the combination therapy can include administering to the subject (e.g., a human patient) one or more additional agents that provide a therapeutic benefit to the subject who has, or is at risk of developing, a demyelinating disorder. In some embodiments, the polyclonal IgG and the one or more additional agents are administered at the same time. In other embodiments, the polyclonal IgG is administered first in time and the one or more additional agents are administered second in time. In some embodiments, the one or more additional agents are administered first in time and the polyclonal IgG is administered second in time. The polyclonal IgG can replace or augment a previously or currently administered therapy. For example, upon treating with polyclonal IgG, administration of the one or more additional agents can cease or diminish, e.g., be administered at lower levels. In other embodiments, administration of the previous therapy is maintained. In some embodiments, a previous therapy will be maintained until the level of polyclonal IgG reaches a level sufficient to provide a therapeutic effect. The two therapies can be administered in combination.

In some embodiments, the individual receiving a first therapy for a demyelinating disorder, e.g., Interferon Beta 1a (Avonex), Interferon Beta 1b (Rebif), glatiramer acetate (Copaxone), mitoxantrone (Novantrone), azathiprine (Imuran), cyclophosphamide (Cytoxan or Neosar), cyclosporine (Sandimmune), methotrexate, Cladribine (Leustatin), methylprednisone (Depo-Medrol or Solu-Medrol), prednisone (Deltasone), prednisolone (Delta-Cortef), dexamethasone (Medrol or Decadron), adreno-corticotrophic hormone (ACTH), or Corticotropin (Acthar), can also be administered polyclonal IgG. In some embodiments, when the human is administered polyclonal IgG, the first therapy is halted. In other embodiments, the human is monitored for a first pre-selected result, e.g., an improvement in one or more symptoms of a demyelinating disorder (such as increased remyelination), e.g., any of the symptoms of demyelinating disorders described herein. In some embodiments, when the first pre-selected result is observed, treatment with polyclonal IgG is decreased or halted. In some embodiments, the human is then monitored for a second pre-selected result after treatment with polyclonal IgG is halted, e.g., a worsening of a symptom of a demyelinating disorder. When the second pre-selected result is observed, administration of the polyclonal IgG to the human is reinstated or increased, or administration of the first therapy is reinstated, or the human is administered both polyclonal IgG, or an increased amount of polyclonal IgG, and the first therapeutic regimen.

In one embodiment, a human receiving a first therapy for a demyelinating disorder, who is then treated with polyclonal IgG, continues to receive the first therapy at the same or a reduced amount. In another embodiment, treatment with the first therapy overlaps for a time with treatment with polyclonal IgG, but treatment with the first therapy is subsequently halted.

In some embodiments of the invention, a therapeutically effective amount of polyclonal IgG is co-administered with an anti-inflammatory to a patient in need thereof. Anti-inflammatory agents are a well-known class of pharmaceutical agents which reduce inflammation by acting on body mechanisms (Stedman's Medical Dictionary 26 e., Williams and Wilkins, (1995); Physicians Desk Reference 51 ed, Medical Economics, (1997)).

Anti-inflammatory agents useful with the methods of the invention include Non-steroidal Anti-Inflammatory Agents (NSAIDS). NSAIDS typically inhibit the body's ability to synthesize prostaglandins. Prostaglandins are a family of hormone-like chemicals, some of which are made in response to cell injury. Specific NSAIDS approved for administration to humans include naproxen sodium, diclofenac, sulindac, oxaprozin, diflunisal, aspirin, piroxicam, indomethocin, etodolac, ibuprofen, fenoprofen, ketoprofen, mefenamic acid, nabumetone, tolmetin sodium, and ketorolac tromethamine.

Other anti-inflammatory agents useful with the methods of the invention include salicylates, such as, for example, salicyclic acid, acetyl salicylic acid, choline salicylate, magnesium salicylate, sodium salicylate, olsalazine, and salsalate.

Other anti-inflammatory agents useful with the methods of the invention include cyclooxygenase (COX) inhibitors. COX catalyzes the conversion of arachidonate to prostaglandin H2 (PGH2); a COX inhibitor inhibits this reaction. COX is also known as prostaglandin H synthase, or PGH synthase. Two Cox genes, Cox-1 and Cox-2 have been isolated in several species. COX-2 is tightly regulated in most tissues and usually only induced in abnormal conditions, such as inflammation, rheumatic and osteo-arthritis, kidney disease and osteoporosis. COX-1 is believed to be constitutively expressed so as to maintain platelet and kidney function and inter homeostasis. Typical COX inhibitors useful in the methods of the invention include etodolac, celebrex, meloxicam, piroxicam, nimesulide, nabumetone, and rofecoxib.

Preferred anti-inflammatory agents that can be incorporated into a polymer matrix for administration in the methods of the invention include: Isonixin, Amtolmetin Guacil, Proglumetacin, Piketoprofen, Difenamizole, Epirizole, Apazone, Feprazone, Morazone, Phenylbutazone, Pipebuzone, Propyphenazone, Ramifenazone, Thiazolinobutazone, Aspirin, Benoiylate, Calcium Acetylsalicylate, Etersalate, Imidazole Salicylate, Lysine Acetyisalicylate, Morpholine Salicylate, 1-Naphthyl Salicylate, Phenyl Acetysalicylate, Ampiroxicam, Droxicam, S-Adenosylmethionine, Amixetine, Benzydamine, Bucolome, Difenpiramide, Emorfazone, Guaiazulene, Nabunetone, Nimesulide, Proquazone, Superoxide Dismutase, and Tenidap.

Anti-inflammatory agents that can be appended to a polymer for administration in the methods of the invention include: Etofenamate, Talniflumate Terofenamate, Acemetacin, Alclofenac, Bufexamac, Cinmetacin, Clopirac, Felbinac, Penclozic Acid, Fentiazac, Ibufenac, Indomethacin, Isofezolac, Isoxepac, Lonazolac, Metiazinic Acid, Mofezolac, Oxametacine, Pirazolac, Sulindac, Tiaramide, Tolmetin, Tropesin, Zomepirac, Bumadizon, Butibufen, Fenbufen, Xenbucin Clidanac, Ketorolac, Tinoridine, Benoxaprofen, Bermoprofen, Bucloxic Acid, Fenoprofen, Flunoxaprofen, Flurbiprofen, Tbuprofen, Tbuproxam, Indoprofen, Ketoprofen, Loxoprofen, Naproxen, Oxaprozin, Pirprofen, Pranoprofen, Prodznic Acid, Suprofen, Tiaprofenic Acid, Zaltoprofen, Benzpiperylon, Mofebutazone, Oxyphenbutazone, Suxibuzone, Acetaminosalol, Parsalmide, Phenyl Salicylate, Salacetamide, Salicylsulfuric Acid, Isoxican, Lomoxicam, Piroxicam, Tenoxicam, .epsilon.-Acetamidocaproic Acid, Bendazac, .alpha.-Bisabolol, Paranyline, Perisoxal, and Zileuton.

Anti-inflammatory agents that can be incorporated into a polymer backbone for administration in the methods of the invention include: Enfenamic Acid, Aceclofenac, Glucametacin, Alminoprofen, Caiprofen, Xinoprofen, Salsalate, 3-Amino-4-hydroxybutyric Acid, Ditazol, Fepradinol, and Oxaceprol.

Anti-inflammatory agents that possess suitable ortho functionality to be incorporated into the backbone of a polymer of formula (I) as described herein include: Flufenamic Acid, Meclofenamic Acid, Mefenamic Acid, Niflumic Acid, Tolfenamic Acid, Amfenac, Bromfenac, Diclofenac Sodium, Etodolac, Bromosaligenin, Diflunisal, Fendosal, Getitisic Acid, Glycol Salicylate, Salicilic Acid, Mesalamine, Olsalazine, Salicylamide O-Acetic Acid, Sulfasalazine, For any anti-inflammatory agent referred to herein by a trade name it is to be understood that either the trade name product or the active ingredient possessing anti-inflammatory activity from the product can be used. Additionally, preferred agents identified herein for incorporation into a polymer backbone can also preferably be appended to a polymer or can be incorporated into a polymer matrix. Preferred agents that can be appended to a polymer can also preferably be incorporated into a polymer matrix.

Examples

Examples are provided below to illustrate the present invention. These examples are not meant to constrain the present invention to any particular application or theory of operation.

Example 1: Investigation of IVIG Effect on Schwann Cells

The direct effect of human serum-derived polyclonal immunoglobulins on Schwann cell homeostasis, differentiation, and maturation as demonstrated through various molecular and cellular variables was investigated using three models: 1) a primary rat Schwann cell culture model; 2) a p57kip2 suppressed Schwann cell model; and 3) a co-culture of PNS neurons and myelinating Schwann cells.

1.1. Preparation of the Rat Schwann Cell Model 1:

In this model, naive primary Schwann cells (SCs) isolated from the sciatic nerves of newborn rats were cultured. At this stage, SCs are immature and have not yet initiated differentiation processes. In culture, they do not progress along their differentiation program and remain proliferative but immature, most likely due to the presence of intrinsic differentiation inhibitors (Heinen et al., 2008a).

1.2. Preparation of P57/Kip2 Suppressed Schwann Cell Model 2:

The present inventors have identified the p57kip2 gene as a novel intrinsic inhibitor of myelinating glial cell differentiation, maturation and myelination. It has been demonstrated that long-term shRNA dependent suppression of the p57kip2 gene uncouples primary SC differentiation from axonal contact. This was revealed by cell cycle exit, altered SC morphology as well as induced myelin expression (Küry et al., 2002; Heinen et al., 2008a; Heinen et al., 2008b). In this second model, p57kip2 suppressed SC was used for comparison with control transfected cells, i.e. non-differentiating cells. This culture system provides the unique opportunity to observe SC differentiation and maturation in vitro in the absence of axons in a quantitative way.

1.3. Preparation of a Co-Culture of PNS Neurons and Myelinating Schwann Cells—Model 3:

In this model, myelinating neuron/SC co-cultures were generated. Culture preparations were made from embryonic Wistar rat or C57/BL6 mouse dorsal root ganglia containing both immature sensory neurons and Schwann cell precursors of the PNS. This co-culture simulates the in vivo situation and offers the possibility of studying the final wrapping/myelination process and whether this complex interaction can be influenced by immunoglobulin administration. Optimization of the co-culture conditions and preparations was done according to established protocols used in the inventors' laboratory or the protocol published from Päiväläinen et al., (2008) with some modifications. IVIG stimulation was performed in parallel to initiation of the myelination process with dialysed IGIV/buffer preparations. IGIV/buffer dialysis was performed against cell culture medium without supplements. All experiments were performed with one concentration of IGIV: 20 mg/ml. The duration of stimulation was determined by analyzing the myelination kinetics (internode formation) after 3 and 6 days following addition of dialysed IGIV/buffer.

1.4. Cell Morphology:

Cell morphology was investigated in model 1 (rat SCs in culture) and model 2 (p57kip2-suppressed SCs) for up to 9 days with stimulation by 10 mg/ml and 20 mg/ml of IVIG for model 1 (to observe dose dependency) and up to 7 days stimulation (9 days transfection) for model 2. Experiments were performed with both non-dialysed and dialysed IGIV and buffer preparations. IVIG and buffer dialysis was performed against cell culture medium without supplements. All model 2 experiments were performed with one concentration of dialysed IGIV (20 mg/ml). In model 2, the cell growth and differentiation kinetics was also determined by measuring the cell protrusion length after 3 and 7 days of stimulation with dialysed IVIG.

1.5. Cell Death/Proliferation:

Cell death/proliferation was investigated in model 1 after 2 days stimulation with non-dialyzed and dialyzed IVIG/buffer preparations. IVIG/buffer dialysis was performed against cell culture medium without supplements. All experiments were performed with one concentration of IVIG (20 mg/ml). Two assays for measuring cell proliferation were employed: immunocytochemical staining against the Ki-67 antigen and imunocytochemical staining against BrdU. Ki-67 antigen is a nuclear protein which serves as a cellular marker for proliferation. BrdU (bromodeoxyuridine) is a nucleotide analogue of thymidine used for labeling of proliferating cells. Immunocytochemical staining against caspase-3 was employed as an apoptosis marker. Caspase-3 is a protease activated in apoptotic cells and therefore used as a cell death marker. Cells were fixed after two different BrdU-pulse durations of 8 h and 24 h.

1.6. Gene Expression:

Gene expression was analyzed in model 1 (rat SCs in culture—section 1.1) and model 2 (p57kip2-suppressed SCs—section 1.2) exposed for up to 9 days stimulation for model 1 and 7 days stimulation (9 days transfection) for model 2 using both non-dialyzed and dialyzed IVIG/buffer preparations. Dialysed SYNAGIS preparations were used as a IgG1 control on naïve SCs (model 1). IVIG/buffer/SYNAGIS dialysis was performed against cell culture medium without supplements. All experiments were performed with one concentration of IVIG: 20 mg/ml. Transcription of myelin genes ($P_0$, MBP) and Fc receptors (CD64, CD32 and CD16) were measured using real-time RT-PCR.

Example 2: Schwann Cell Responds to Incubation with IVIG 2.1. Morphology:

IVIG treatment was observed to affect Schwann cell morphology. SCs cultured in the presence of 10 mg/ml IVIG, and to a larger extent, in the presence of 20 mg/ml IVIG, appeared to have larger somata and nuclei. It is currently unclear whether this is a direct impact on SC shape and cytoskeleton or adhesion properties, a result from different cell densities, or is reflective of discrete cell surface alterations possibly connected to the IVIG binding site(s) on the cell surface.

Significantly accelerated growth of cellular protrusions was measured upon stimulation with IGIV using model 2 (p57kip2 suppression). This effect was observed only in the early stages of the differentiation process, indicating an IVIG effect on the differentiation kinetics of the Schwann cells. To explain, the growth of cellular protrusions is a maturation parameter which was found to be dependent on suppressed p57kip2 levels. On the other hand, no effect on actin filament assembly and structure could be observed after IVIG stimulation as revealed by TRITC conjugated phalloidin stainings.

Figure 1A:
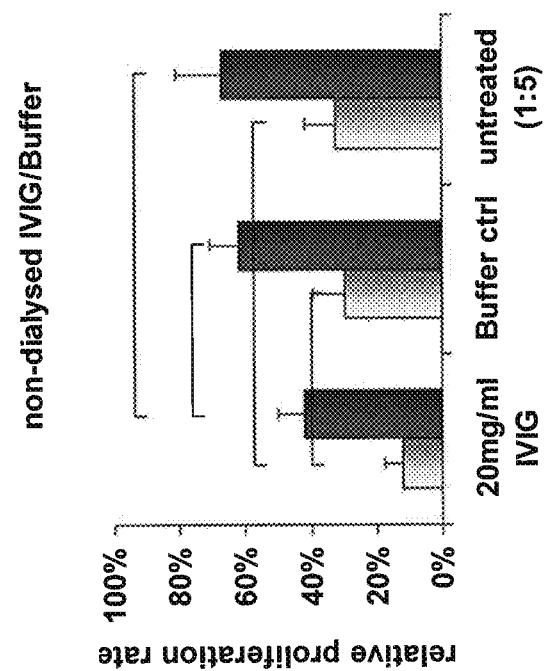
Figure 2B:
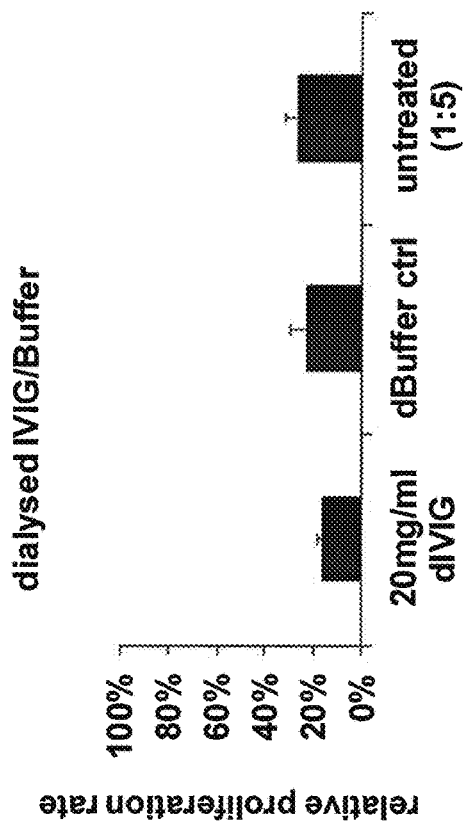
Figure 2A:
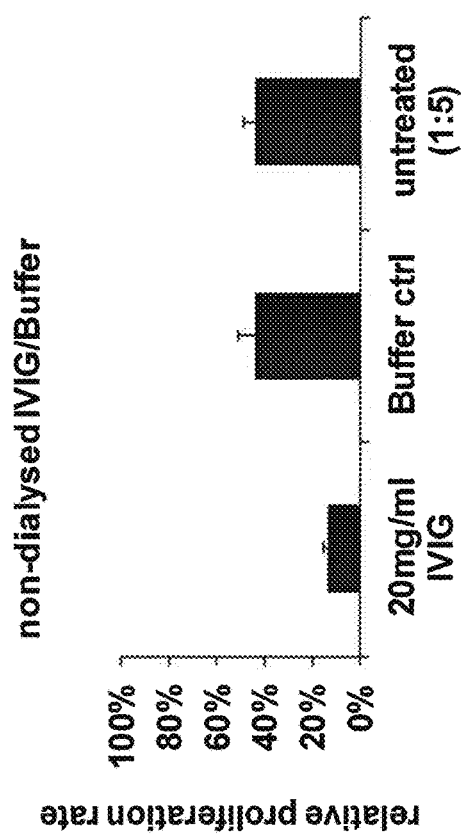
Figure 5:
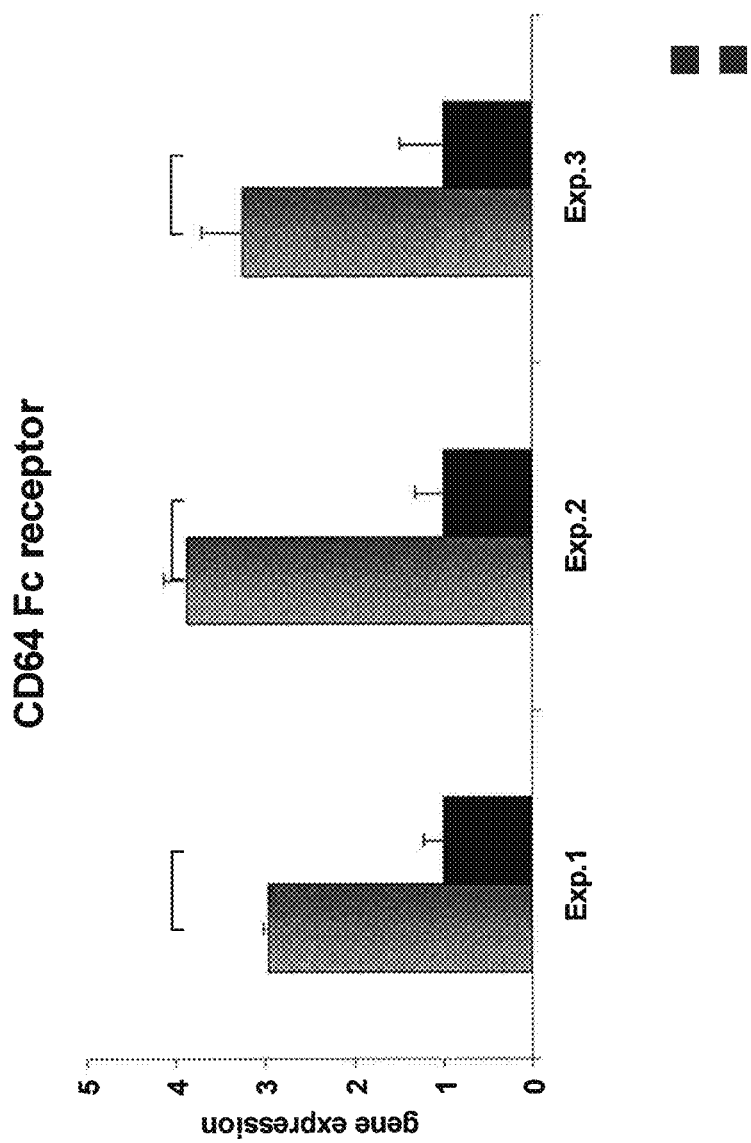
FIG. 5 shows the expression levels of CD64 Fc receptor in p57kip2 suppressed Schwann cells as compared to control transfected Schwann cells (without p57kip2 suppression). Neither group of Schwann cells were exposed to IVIG/buffer formulations.
Figure 6B:
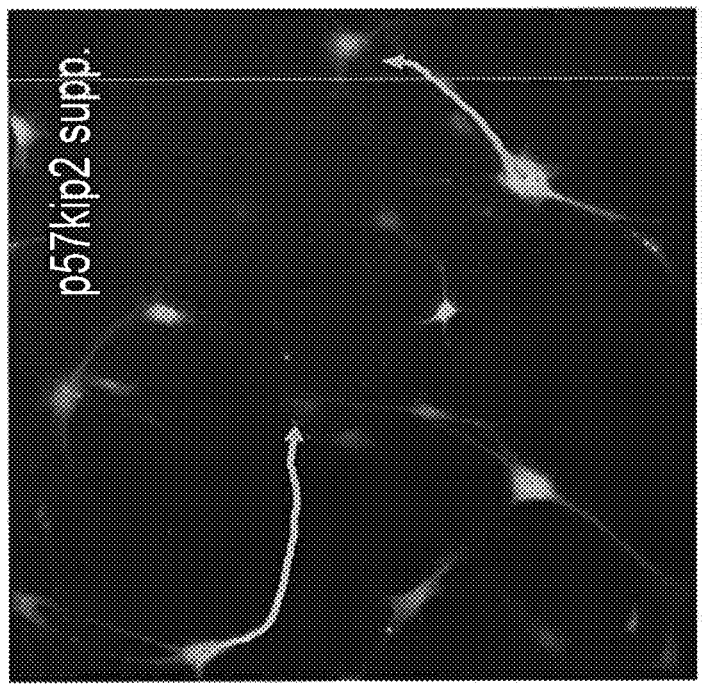
FIG. 6A and FIG. 6B show fluorescent images of p57kip2 suppressed Schwann cells (FIG. 6B) and control transfected cells (FIG. 6A) after stimulation with 20 mg dialyzed IVIG/buffer formulations. The location and length of cellular processes are indicated by the arrows superimposed onto the fluorescent images.
Figure 6A:
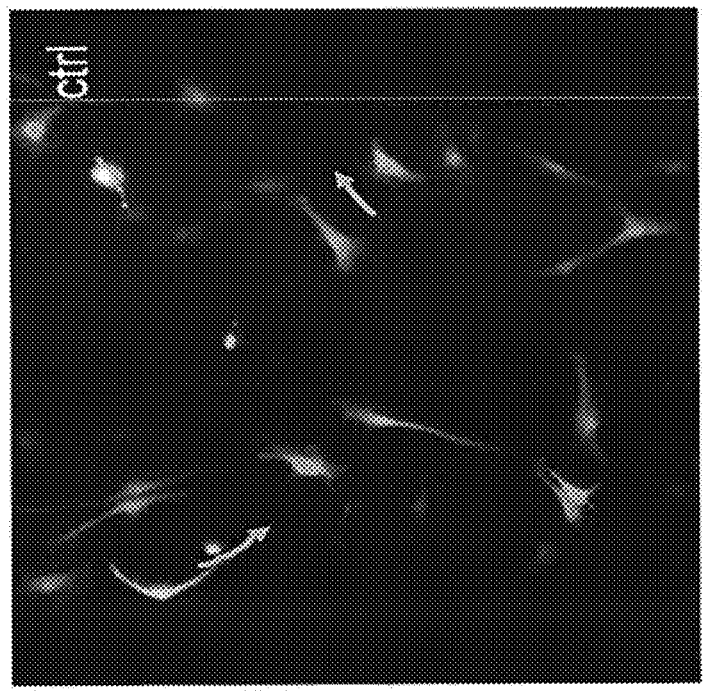
Figure 7A:
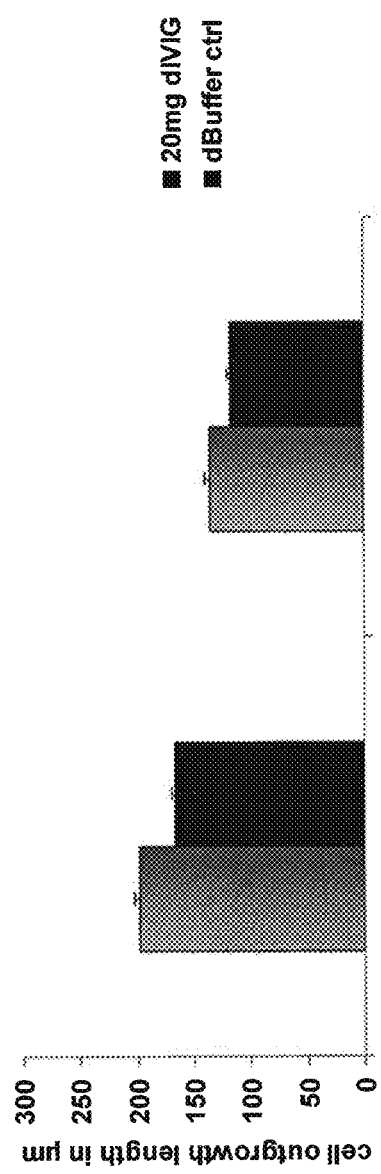
FIG. 7A, FIG. 7B, FIG. 7C and FIG. 7D show a graph of the cell outgrowth length for p57kip2 suppressed Schwann cells and control transfected cells (FIG. 7A) after 3 days of stimulation with dialysed IVIG/buffer formulations (5 days suppression) along with the respective fluorescent images of the p57kip2 suppressed Schwann cells stimulated with 20 mg of IVIG (FIG. 7B), p57kip2 suppressed Schwann cells stimulated with buffer (FIG. 7C), control transfected cells treated with 20 mg IVIG (FIG. 7D), and control transfected cells treated with buffer (FIG. 7E).
Figure 7D:
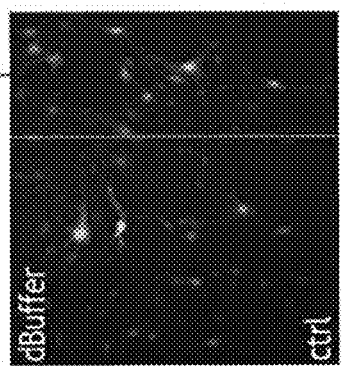
Figure 7E:
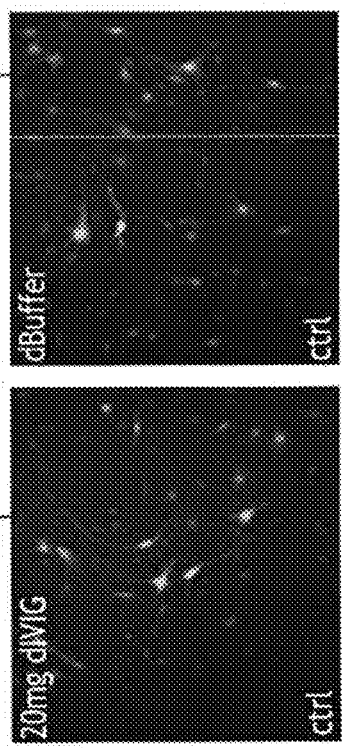
Figure 7B:
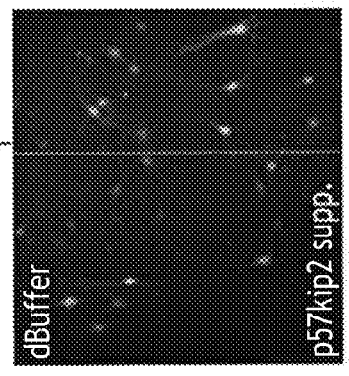
Figure 7C:
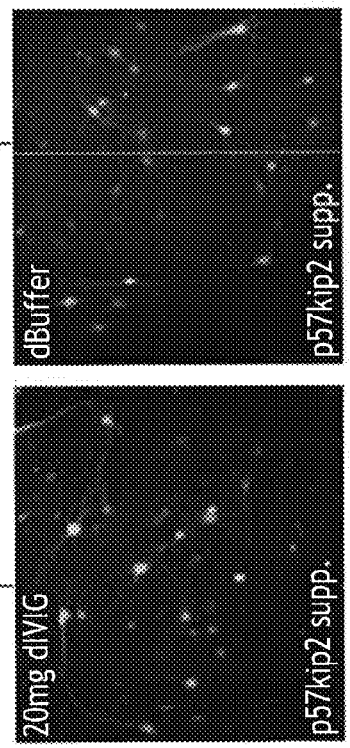
Figure 9:
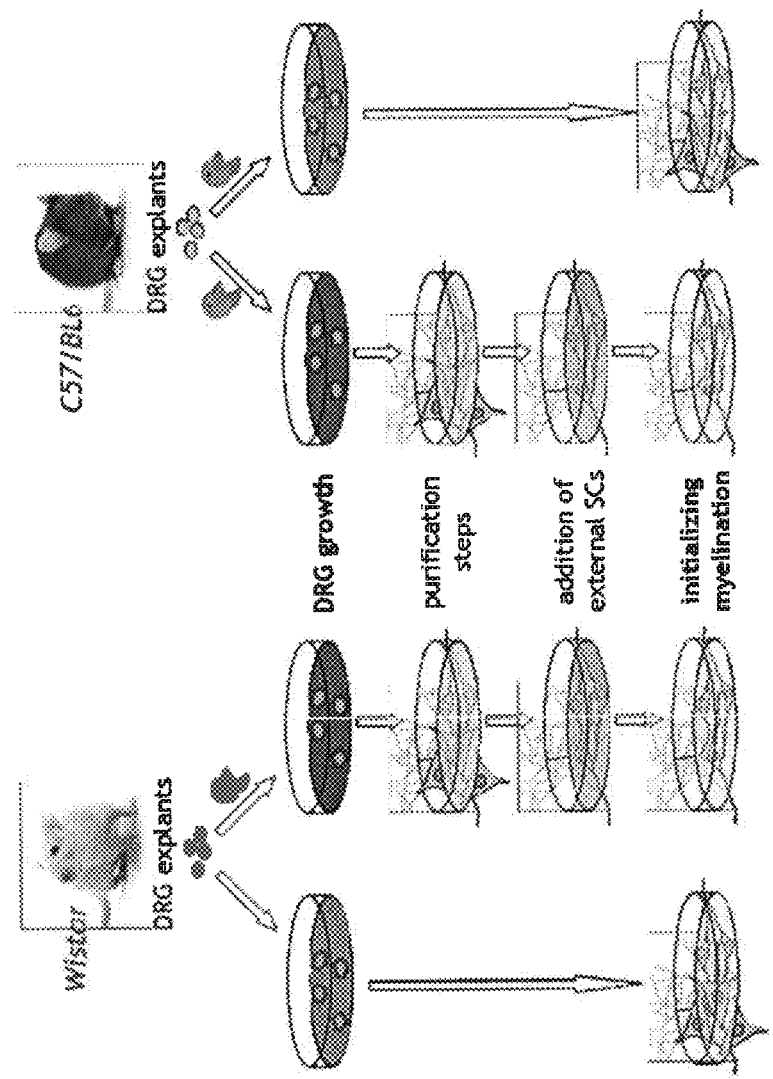
FIG. 9 is a flow diagram of the process for establishing a cocultue of PNS neurons (rat dorsal root ganglion) and myelinating Schwann cells.

2.2. Cell Death/Proliferation (Model 1):

After stimulation with non-dialyzed IVIG (20 mg/ml) preparations, the proliferation rate of naïve SC was significantly reduced, as revealed by assays using proliferation markers BrdU and Ki-67. See FIGS. 1-2. The IVIG-dependent effect on the proliferation rate was diminished with IVIG dialysis, but remained statistically significant thereafter. There is currently no evidence of induction of apoptosis after treatment with IVIG based on the negative staining for caspase-3.

2.3. Gene Expression:

Stimulation of non-transfected SCs (model 1) with non-dialyzed and dialyzed IVIG/buffer preparations led to slight upregulation of $P_0$ and strong upregulation of the MBP genes within the first 3 days of treatment, but not after longer incubation periods. Stimulation of p57kip2 suppressed cells (model 2) with non-dialyzed and dialyzed IVIG/buffer preparations also led to similar results regarding myelin gene expression. The expression and upregulation of both myelin genes were significantly stronger in the p57kip2-suppressed cells than in the control transfected cells. Observations of the gene regulation of Fc receptors showed that Schwann cells express CD64 and CD32 and that long term suppression for p57kip2 leads to significant upregulation of these genes. There was a detectable level of CD64 Fc receptor expression in immature SCs. In differentiating Schwann cells (upon suppression of the intrinsic inhibitor p57kip2), CD64 levels were significantly increased with IVIG stimulation.

Importantly, the monoclonal IgG1 controls (Synagis, Avastin and Herceptin) showed no significant effect on myelin gene expression. Stimulation of p57kip2 suppressed cells (model 2) with non-dialysed and dialysed IVIG/buffer preparations induced myelin gene expression to a similar extent. Again MBP expression was strongly induced upon IVIG stimulation whereas P0 expression was mildly induced by the treatment. Note that myelin gene induction could be observed during a period of seven days of stimulation and was therefore not limited to early phases. Furthermore, the expression of the p57kip2 gene was found to encode an intrinsic inhibitor of Schwann cell differentiation and was significantly lowered in control transfected (non-differentiating) cells.

Observations of the gene regulation of all known Fcγ receptors showed that Schwann cells express the CD64 Fc receptor. In differentiating Schwann cells (model 2), CD64 levels were significantly increased in comparison to control transfected (non-differentiating) cells. Regulation of the CD64 receptor expression in response to IVIG stimulation could not be observed. Of note, effects of the non-dialysed buffer control were observed in all the gene expression experiments performed. This effect was, however, diminished after dialysis. Further gene expression analyses were therefore performed with dialysed IVIG preparations only.

2.4. Summary of Findings:

In the first 18 months of the investigation, it was discovered that primary SCs respond to IVIG incubation with altered cell morphology accompanied by an accelerated growth of cellular protrusions in early stages of the differentiation process. Incubation with IVIG was also found to reduce Schwann cell proliferation without affecting cell survival. Furthermore, expression of two major myelin genes, $P_0$ and MBP, was induced in immature as well as differentiating SCs following stimulation with IVIG. Data shows that primary rat Schwann cells were express the CD64 Fc receptor and that in differentiating Schwann cells (upon suppression of the intrinsic inhibitor p57kip2), CD64 levels were significantly increased with exposure to IVIG. The evidence also provides strong indications for an upregulation of Fc receptors (in particular CD64) in differentiating SCs. Furthermore, a specific binding of the human IVIGs on the Schwann cell surface was shown.

These findings support the hypothesis that SCs might exhibit immune competence. Reduced proliferating rate with no signs of apoptosis as well as the induction of myelin genes, combined with accelerated growth of cellular protrusions, suggest a promotion of the differentiation process in the immature SC by IVIG. These are the first in vitro results demonstrating that Schwann cells are not only able to respond to but also to specifically bind immunoglobulins and that IVIG stimulation can promote Schwann cell precursor maturation.

Example 3: Gene Expression

For further examination of the IVIG dependent effects on differentiating (p57kip2 suppressed cells, model 2) and non-differentiating (control suppressed cells, model 2) Schwann cell gene expression we collected 16 RNA samples from 4 independent experiments for a GeneChip Array analysis (performed by Miltenyi Biotec, Germany). Sample validation was performed by determination of expression levels of MBP, $P_0$, p57kip2 and CD64 genes.

Statistical and functional analysis was performed. Genes that were identified as significantly up- or down-regulated upon treatment with IVIG are provided in Tables 1 and 2. Future aims are at further gene identification as well as validation of the obtained results.

TABLE 1

Comparison of non-differentiating Schwann cells +/− IVIG

| Up regulated genes after treatment (gene sequence name) | Down regulated genes after treatment (gene sequence name) |
|---|---|
| Tyrp1 | RGD1562551 |
| Tyrp1 | Ctnna2 |
| Col24a1 | Olr832 |
| Fat3 | Phgr1 |
| Tmem72 | RGD1566220 |
| Tesc | Nedd9 |
| Il18 | Slc12a3 |
| Mt1a | Arhgef9 |
| Slc40a1 | Gckr |
| Asgr1 | TC636329 |
| LOC678704 | A_64_P023581 |
| TC609365 | Ptprr |
| Bcl6b | Olr749 |
| A_64_P063062 | Nebl |
| Npas2 | RGD1562545 |
| Gpx2 | Hes5 |
| Matn1 | Mpzl2 |
| A_64_P022503 | Ezr |
| Fbxo32 | Cryab |
| Pls1 | Fcgr2b |
| A_64_P094596 | |
| A_64_P025678 | |
| Olig1 | |
| Sox2 | |
| Plp1 | |

TABLE 2

Comparison of differentiating Schwann cells +/− IVIG

| Up regulated genes after treatment (gene sequence name) | Down regulated genes after treatment (gene sequence name) |
|---|---|
| ENSRNOT00000064975 | XM_346212 |
| Zfp334 | XR_009266 |
| Mmp25 | LOC688695 |

TABLE 2-continued

Comparison of differentiating Schwann cells +/− IVIG

| Up regulated genes after treatment (gene sequence name) | Down regulated genes after treatment (gene sequence name) |
|---|---|
| A_64_P117674 | Ak3l1 |
| A_64_P151655 | A_64_P163956 |
| A_44_P386999 | |
| Olig1 | |
| Sox10 | |
| Hes5 | |

In order to confirm the observed induction of myelin gene expression (in particular $P_O$ and MBP) at protein level, we performed Western-blot analysis on p57kip2 suppressed versus control suppressed cells (model 2) after treatment with dialysed IVIG/buffer. We could demonstrate that in differentiating Schwann cells protein levels of $P_O$ and to a lesser extent of MBP were increased after IVIG treatment.

Example 4: Immune-Related Proteins

It was important to confirm direct IVIG binding to the Schwann cell surface. Applying an anti-human Fab-specific F(ab)'$_2$ and anti-human Fcγ-specific F(ab)'2 antibodies, it was shown that human immunoglobulins in the IVIG specifically bound to the Schwann cell surface. Live Schwann cells in culture were stimulated with IVIG, washed, fixed and then separately stained against human Fab fragments, human Fcγ fragments or against both epitopes in combination of a double-staining. A specific surface binding could be localized within the perinuclear region of the cells. These binding studies were performed with naïve Schwann cells (model 1) using IVIG and IgG1 controls (Avastin and Herceptin) as well as with differentiating Schwann cells (model 2) using IVIG. In order to address the question of whether CD64 receptor protein is also expressed on the Schwann cell surface, staining experiments with two anti-CD64 antibodies have been initiated.

In order to determine whether CD64 receptor protein was also expressed on the Schwann cell surface staining experiments with two anti-CD64 antibodies were performed. One anti-CD64 antibody appeared to bind specifically to the rat CD64 receptor on the Schwann cells and diffuse receptor staining was distributed over the cell surface of the non-differentiating cells. In comparison, the receptor staining on differentiating cells was concentrated to the cell soma above the perinuclear region. The detected CD64 signals did not coincide with the IVIG binding signals (comparison of immunological stainings).

Example 5: Internode Formation

In order to improve efficiency and reproducibility of the in vitro myelination model (model 3), a number of experimental improvement steps using DRG cultures derived C57/BL6 mouse embryos were performed and established. To this end, the protocol according to Päiväläinen et al. (2008) was modified and can now be used to study the effects of IVIG application on axon/Schwann cell interactions. IVIG stimulation (20 mg/ml) was performed concomitant to the initiation of the myelination process using dialysed IGIV/buffer preparations.

After determination of the optimal time point for the analysis at 7 days upon initiation of myelinisation, a statistically significant number of IVIG stimulation experiments (n=9) were performed. In order to evaluate the ability of immunoglobulin treatment to modulate the generation of myelin sheaths (internode formation), the number of internodes (normalizing to the whole number of nuclei in the co-culture) of IVIG treated were compared to the number of internodes in control co-cultures. Although a trend towards slightly increased internode densities could be observed, no statistically significant difference in myelin segment formation was detected after treatment.

Example 6: In Vivo Nerve Repair Paradigm 6.1. Summary

In order to translate in vitro findings based on primary rat Schwann cell cultures to an in vivo paradigm, chronic peripheral nerve lesions were induced in adult rats treated with IVIG or control buffer during a so called "nerve regeneration period". Sciatic nerves were transected and, by means of suturing religation of nerve ends, nerve regeneration was prevented for a period of three months. After this degeneration period, nerves were ligated to allow regeneration to take place and IVIG or buffer was administered (i.p. injections). Nerves were allowed to regenerate for another three months until the animals were sacrificed.

The above-described surgical approach on Schwann cells was used to determine whether IVIG stimulation can repair the activity of injured peripheral nerves. During the three months regeneration (and IVIG/buffer treatment) period a number of functional tests were performed on live rats. Afterwards animals were sacrificed and sciatic nerves were dissected, fixed and embedded for morphological and immunohistochemical future analyses aiming at the description of Schwann cell/myelin and axonal reactions. Preliminary results were acquired from the functional analyses. These preliminary findings indicate that differences between the two groups (IVIG vs. buffer treated animals) exist. Specifically, IVIG treated animals displayed longer and broader footprint areas (contact zones between foot and floor) as compared to buffer treated animals. These footprint areas also gradually increased during the treatment period and this was accompanied with an increased landing pressure (corresponding to the force that is used by the leg to make a step or to the pressure the foot exerts to the surface). Overall these first preliminary data suggest that IVIG treated animals experience an accelerated normalization of walking behavior and an increased strength in their leg usage.

6.2. Methods

IVIG dependent effects on Schwann cell survival were investigated. Specifically, a previously established chronic peripheral nerve denervation model (Fu and Gordon; J Neurosci 1995) was used to study the proliferation as well as remyelination and axonal regeneration in denervated nerve segments in vivo. This in vivo model features similar nerve conditions to those observed in many human nerve pathologies. This in vivo model also provides the advantage of focusing on regenerative events only as degeneration processes (i.e., immune reactions are temporally excluded).

For this purpose sciatic nerves of 24 adult Lewis rats were transected and nerve regeneration was prevented by means of surturing religation of the nerve ends. This setup results in chronically injured and denervated nerve segments. Regeneration was prevented for the period of three months after nerve transaction. During this period, no functional tests were performed with the animals.

After three months of degeneration all 24 rats were exposed to a delayed sciatic nerve ligation (anastomosis) in that proximal nerve segments were sutured to the distal nerve segments thereby allowing nerve regeneration to take place. Note that in this chronic setup, the overall regeneration capacity was significantly reduced as compared to acute nerve lesions. During this first three months period axonal and myelin degeneration process were completed.

In a first set of experiments (study 1), the generation of anti-drug antibodies (ADA) and human IgG plasma levels after IVIG application was studied in healthy rats (unlesioned nerves) using ELISA tests. ADA against IVIGs was then monitored in lesioned and treated animals as secondary readout in study 2 (see below).

In a second set of experiments (study 2), Lewis Rats with chronic peripheral nerve lesions was treated with 1 g IVIG/kg body weight (high-dose treatment) following nerve ligation (regeneration period of 3 month). IVIG application was done by means of i.p. injections once every week in the first month and then once every second week in the last two months of the regeneration phase. Control rats with nerve lesions received IVIG formulation buffer injections. Control buffer treated and IVIG treated animal groups comprised of 12 adult female rats each. During the period of IVIG treatment, blood samples were collected from the tail vein in order to monitor ADA and to determine the half-life of human IgG (see study 1). Blood plasma samples were collected every second week prior to treatment.

6.2. Results

In order to test the degree of recovery of function of the target organs after religation of the nerve ends, a weekly set of functional evaluation tests were conducted. Sensory function was evaluated by testing the withdrawal response of toe 4 and 5 after application of a pain stimulus (pinch test with a forceps). Muscle strength and regeneration of muscle fibers were analyzed using the leg spread test. These two functional tests as well as monitoring of the animals' weight (health and wellbeing parameter) were done on a weekly basis. The animals were further subjected to weekly monitoring of footprints and walking tracks (i.e., the "cat walk analysis") to evaluate functional recovery of the sciatic nerves.

At the end of the study, 21 animals were left: 10 animals that received buffer control injections and 11 animals treated with IVIG. All rats were sacrificed and the regenerating peripheral nerve segments, as well as contralateral healthy control nerves were collected for further analysis. For this purpose animals were divided in three groups:

Group I consists of 4 buffer treated and 4 IVIG treated animals. Sciatic nerves segments (healthy and transected) of these animals will be processed for electron microscopy analysis (EM). Apart from determining axonal density (thus measuring regeneration efficiency) this will also include a g-ratio calculation (axonal diameter divided by the diameter of the axon and its myelin sheath) in order to determine remyelination efficiencies. This analysis is currently ongoing. Functional evaluation data of these animals (cat walk data, pinch-test and leg spread behavior) were determined and preliminary results are described below.

Group II consists of 3 buffer treated and 4 IVIG treated animals. Sciatic nerves segments (healthy and transected) of these animals will be used for immunohistochemical stainings (IHC) against axonal, myelin and glial markers in order to determine the degree of cellular redifferentiation and regeneration. Nerves are currently processed and this study is also ongoing. Functional evaluation data of these animals (cat walk data, pinch-test and leg spread behavior) were determined and preliminary results are available are described below.

Group III consists of 3 buffer treated and 3 IVIG treated animals. The transected sciatic nerves segments of these animals displayed no anatomical regeneration signs since the anastomosis did not take place. The functional evaluation data of these animals will not be included in the overall analysis.

A preliminary evaluation of the cat walk data indicates that differences between the two groups (IVIG vs. buffer treated animals) exist. IVIG treated animals displayed longer and broader footprint areas (contact zones between foot and floor) as compared to buffer treated animals. These footprint areas also gradually increased during the treatment period and this was accompanied with an increased landing pressure (corresponding to the force that is used by the leg to make a step or to the pressure the foot exerts to the surface). Overall this data suggest that IVIG treated animals experience an accelerated normalization of walking behavior and an increased strength in their leg usage.

Example 7: Supplemental Studies to Determine the Underyling Mechanisms of IVIG Action To better understand the underlying mechanisms of IVIG action and mechanisms by which IVIGs promote cellular maturation, detailed molecular/cellular investigations on stimulated Schwann cells will be performed.

As outlined above (see 5.1), a GeneChip analysis on non-differentiating and differentiating Schwann cells exposed to IVIG treatment was performed and analyzed. Based upon the newly discovered unregulated and down-regulated genes (Tables 1 and 2), further validation experiments will be conducted using quantitative real-time RT-PCR on selected genes. If necessary and applicable, additional validations using antibodies (Western-blot, immunological stainings as well as ELISA) will be performed. This will be particularly interesting for genes related to immune competence. Of note, this expression analysis will not only be analyzed in order to understand what cellular processes are most IVIG sensitive, it will most likely also serve to define additional marker genes that can be used to monitor and quantify IVIG dependent reactions.

Following establishment of a suitable in vitro myelination assay (model 3), a statistically significant number of IVIG stimulation experiments will be performed. The active time windows and to which extent immunoglobulin treatment can modulate the generation of myelin sheaths (internode formation) will be evaluated.

Using a Cy3 conjugated anti-human Fab antibody, the specific binding of IVIGs to Schwann cell surfaces can be demonstrated. It remains to be shown whether this is due to interaction with the CD64 Fc receptor or whether Schwann cell-specific epitopes are recognized by Fab-mediated binding. For this purpose, Schwann cells (model 1) will either be contacted with Fc and F(ab)2 fractions of papain-digested IVIG or bound IVIGs on Schwann cells will be digested with papain in situ. Furthermore, the application of a FITC-conjugated anti-human Fc antibody in combination with Cy3 conjugated anti-human Fab antibody is expected to result in papain sensitive stainings. Two anti-CD64 antibodies will be applied on non-differentiating and differentiating (model 2) Schwann cells in order to determine whether CD64 is also expressed as a receptor protein on the Schwann cell surface. In case that the IVIG binding is really mediated via this Fc receptor, it will be expected that the CD64 signals coincide with the IVIG binding (immunological stainings). Further to this end, it will be examined whether an increase in CD64 protein levels can be observed as a consequence of the differentiation process (Western-blot).

To provide functional proof for Fc-receptor involvement, pharmacological inhibitors such as 3-(1-Methyl-1H-indol-3-yl-methylene)-2-oxo-2,3-dihydro-1H-indole-5-sulfonamide or Ly294002 interfering with spleen tyrosine kinase (Syk) and phosphatidylinositol-3-kinase (PI3K) will be applied, respectively, prior to IVIG stimulation of naïve Schwann cells (model 1). This will indicate whether these Fc-dependent signaling components are involved in MBP induction (or appropriate marker genes identified in 1.). Furthermore, digested IVIGs will be used to stimulate cultured Schwann cells (model 1) in order to reveal whether Fc or/and Fab fractions are responsible for IVIG specific gene regulations (MBP and other marker genes identified in the gene expression analysis). Finally, shRNA-mediated suppression of CD64 expression in Schwann cells (model 1) can be used to confirm that IVIG binding is CD64 dependent as well as responsible for the IVIG dependent induction of MBP expression (or other marker genes identified in the gene expression analysis).

Standard Schwann cell culture (maintenance and differentiation) conditions feature high fetal calf serum concentrations (up to 10% of volume). It is therefore conceivable that immunoglobulins present in the serum are diminishing IVIG-dependent Schwann cell reactions. To test this, the serum concentration will be reduced to the lower limit needed in order to assure cell survival and differentiation, the Schwann cells stimulated with IVIGs and MBP expression levels (models 1 and 2) as well as morphological parameters measured (model 2).

The present inventors' recent investigations revealed that Schwann cell differentiation is critically dependent of the histone methyltransferase enhancer of zeste homolog 2 (EZH2; Heinen et al., in revision). Upon suppression of EZH2 activity, cultured Schwann cells show dedifferentiation reactions similar to what is observed in nerve pathologies. As part of future investigations, such dedifferentiating Schwann cells will be stimulated with IVIGs to determine expression of Schwann cell marker and myelin genes. The latter of which were shown to be downregulated below control levels. It will be of interest to see whether immunoglobulin treatment is not only able to promote differentiation/maturation reactions (as seen with model 2; i.e. upon suppression of the inhibitory gene p57kip2) but can also interfere with dedifferentiation processes (such as normalization of myelin gene expression levels).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

Arnson, Y., Shoenfeld, Y., Amital, H. (2009). Intravenous immunoglobulin therapy for autoimmune diseases. Autoimmunity 42(6), 553-60.

Asakura, K., Miller, D. J., Pease, L. R. and Rodriguez, M. (1998). Targeting of IgMkappa antibodies to oligodendrocytes promotes CNS remyelination. J. Neurosci. 18, 7700-7708.

Bhatheja, K. and Field, J. (2006). Schwann cells: origins and role in axonal maintenance and regeneration. Int. J. Biochem. Cell Biol. 38(12):1995-9.

Bieber, A., Asakura, K., Warrington, A., Kaveri, S. V., and Rodriguez, M. (2000). Antibody-mediated remyelination: relevance to multiple sclerosis. Mult. Scler. 6 Suppl 2, S1-S5.

Bieber, A., Asakura, K., Warrington, A., Kaveri, S. V., and Rodriguez, M. (2000). Antibody-mediated remyelination: relevance to multiple sclerosis. Mult. Scler. 6 Suppl 2, S1-S5.

Burstyn-Cohen, T., Frumkin, A., Xu, Y. T., Scherer, S. S., and Klar, A. (1998). Accumulation of F-spondin in injured peripheral nerve promotes the outgrowth of sensory axons. J. Neurosci., 18(21), 8875-8885.

Burstyn-Cohen, T., Frumkin, A., Xu, Y. T., Scherer, S. S., and Klar, A. (1998). Accumulation of F-spondin in injured peripheral nerve promotes the outgrowth of sensory axons. J. Neurosci., 18(21), 8875-8885.

Fu, S. Y. and Gordon, T. (1995b). Contributing factors to poor functional recovery after delayed nerve repair: Prolonged denervation. J. Neurosci., 15(5), 3886-3895.

Heinen, A., Kremer, D., Hartung, H. P., and Küry P. (2008a). p57(kip2)'s role beyond Schwann cell cycle control. Cell Cycle 7, 2781-2786.

Heinen, A., Kremer, D., Gottle, P., Kruse, F., Hasse, B., Lehmann, H., Hartung, H. P., and Küry, P. (2008b). The cyclin-dependent kinase inhibitor p57kip2 is a negative regulator of Schwann cell differentiation and in vitro myelination. Proc. Natl. Acad. Sci. U. S. A 105, 8748-8753.

Küry, P., Greiner-Petter, R., Comely, C., Jürgens, T. and Müller, H. W. (2002). Mammalian Achaete Scute Homolog 2 Is Expressed in the Adult Sciatic Nerve and Regulates the Expression of Krox24, Mob-1, CXCR4, and p57kip2 in Schwann Cells. J. Neurosci. 22, 7586-7595.

Lin, H. H., Spies, J. M., Lu, J. L. and Pollard, J. D. (2007), Effective treatment of experimental autoimmune neuritis with human immunoglobulin. J. Neurol Sci.; 256:61-7.

Nakahara, J., Seiwa, C., Shibuya, A., Aiso, S. and Asou, H. (2003). Expression of Fc receptor for immunoglobulin M in oligodendrocytes and myelin of mouse central nervous system. Neurosci. Lett. 337, 73-76.

Negi, V. S., Elluru, S., Siberil, S. Graff-Dubois, S., Mouthon, L., Kazatchkine, M. D., Lacroix-Desmazes, S., Bayry, J. and Kaveri, S. V. (2007). Intravenous immunoglobulin: an update on the clinical use and mechanisms of action. J. Clin. Immunol. 27:233.

Päiväläinen, S., Nissinen, M., Honkanen, H., Lahti, O., Kangas, S. M., Peltonen, J., Peltonen, S. and Heapea, A. M. (2008). Myelination in mouse dorsal root ganglion/Schwann cell cocultures. Mol. Cell. Neurosci. 37, 568-578.

Handbook of Development Neurotoxicology eds. Slikker et al. (1998), Academic Press, San Diego.

Vargas, M. E., Watanabe, J., Singh, S. J., Robinson, W. H. and Barres, B. A. (2010). Endogenous antibodies promote rapid myelin clearance and effective axon regeneration after nerve injury. Proc. Natl. Acad. Sci. U. S. A 107 (26), 11993-11998.

Warrington, A. E., Bieber, A. J., Ciric, B., Pease, L. R., Van, K., V, and Rodriguez, M. (2007). A recombinant human IgM promotes myelin repair after a single, very low dose. J. Neurosci. Res. 85, 967-976.

What is claimed is:

1. A method of promoting myelination of a peripheral nerve cell by a Schwann cell comprising contacting the Schwann cell with an amount of polyclonal IgG sufficient to promote myelination of the peripheral nerve cell by the Schwann cell, wherein the peripheral nerve cell is from a mammal with a demyelinating peripheral neuropathy, wherein the demyelinating peripheral neuropathy is selected from the group consisting of a trauma-induced demyelinating neuropathy, a toxin-induced demyelinating neuropathy, and an inherited demyelinating neuropathy and excludes Guillain-Barré syndrome, chronic demyelinating polyneuropathy and multifocal motor neuropathy.

2. The method of claim 1, wherein the peripheral nerve cell is in vitro.

3. The method of claim 1, wherein the peripheral nerve cell is in vivo.

4. The method of claim 3, wherein the peripheral nerve cell is in a mammal with a demyelinating peripheral neuropathy.

5. The method of claim 4, wherein said inherited neuropathy is not infection-mediated.

6. The method of claim 4, wherein the mammal is human.

7. The method of claim 4, wherein the polyclonal IgG is administered locally.

8. The method of claim 7, wherein the polyclonal IgG is administered subcutaneously, intramuscularly, or intradermally.

9. The method of claim 4, wherein the polyclonal IgG is administered systemically.

10. The method of claim 9, wherein the polyclonal IgG is administered parenterally, intra-arterially, or intravenously.

11. The method of claim 4, wherein an anti-inflammatory agent is co-administered with the polyclonal IgG to the mammal.

12. The method of claim 11, wherein the anti-inflammatory agent is adrenocorticotropic hormone.

13. The method of claim 11, wherein the anti-inflammatory agent is a corticosteroid.

14. The method of claim 11, wherein the anti-inflammatory agent is an interferon.

15. The method of claim 11, wherein the anti-inflammatory agent is glatiramer acetate.

16. The method of claim 11, wherein the anti-inflammatory agent is a non-steroidal anti-inflammatory drug.

17. The method of claim 4, wherein the polyclonal IgG is administered weekly.

18. The method of claim 4, wherein the polyclonal IgG is administered biweekly.

19. The method of claim 4, wherein the polyclonal IgG is administered monthly.

20. The method of claim 4, wherein the polyclonal IgG is administered to the mammal at a dose of about 0.05 to 5 g per kg of patient body weight.

21. The method of claim 20, wherein the polyclonal IgG is administered to the mammal at a dose of about 0.5 to 2 g per kg of patient body weight.

22. A method of promoting the differentiation of an immature Schwann cell into a myelinating state comprising contacting the Schwann cell with polyclonal IgG in an amount sufficient to induce the Schwann cell differentiation, wherein the Schwann cell is from a mammal with a demyelinating peripheral neuropathy, wherein the demyelinating peripheral neuropathy is selected from the group consisting of a trauma-induced demyelinating neuropathy, a toxin-induced demyelinating neuropathy, and an inherited demyelinating neuropathy and excludes Guillain-Barré syndrome, chronic demyelinating polyneuropathy and multifocal motor neuropathy.

23. The method of claim 22, wherein the Schwann cell is in vitro.

24. The method of claim 22, wherein the Schwann cell is in vivo.

25. The method of claim 24, wherein the Schwann cell is in a mammal with a demyelinating peripheral neuropathy.

26. The method of claim 25, wherein said inherited neuropathy is not infection-mediated.

27. The method of claim 25, wherein the mammal is human.

28. The method of claim 25, wherein the polyclonal IgG is administered locally.

29. The method of claim 28, wherein the polyclonal IgG is administered subcutaneously, intramuscularly, or intradermally.

30. The method of claim 25, wherein the polyclonal IgG is administered systemically.

31. The method of claim 30, wherein the polyclonal IgG is administered parenterally, intra-arterially, or intravenously.

32. The method of claim 25, wherein an anti-inflammatory agent is co-administered with the polyclonal IgG to the mammal.

33. The method of claim 32, wherein the anti-inflammatory agent is adrenocorticotropic hormone.

34. The method of claim 32, wherein the anti-inflammatory agent is a corticosteroid.

35. The method of claim 32, wherein the anti-inflammatory agent is an interferon.

36. The method of claim 32, wherein the anti-inflammatory agent is glatiramer acetate.

37. The method of claim 32, wherein the anti-inflammatory agent is a non-steroidal anti-inflammatory drug.

38. The method of claim 25, wherein the polyclonal IgG is administered weekly.

39. The method of claim 25, wherein the polyclonal IgG is administered biweekly.

40. The method of claim 25, wherein the polyclonal IgG is administered monthly.

41. The method of claim 25, wherein the polyclonal IgG is administered to the mammal at a dose of about 0.05 to 5 g per kg of patient body weight.

42. The method of claim 41, wherein the polyclonal IgG is administered to the mammal at a dose of about 0.5 to 2 g per kg of patient body weight.

43. A method of promoting the production of myelin by a Schwann cell comprising contacting the Schwann cell with an amount of polyclonal IgG sufficient to upregulate MBP genes, wherein the Schwann cell is from a mammal with a demyelinating peripheral neuropathy, wherein the demyelinating peripheral neuropathy is selected from the group consisting of a trauma-induced demyelinating neuropathy, a toxin-induced demyelinating neuropathy, and an inherited demyelinating neuropathy and excludes Guillain-Barré syndrome, chronic demyelinating polyneuropathy and multifocal motor neuropathy.

44. The method of claim 43, wherein the Schwann cell is in vitro.

45. The method of claim 43, wherein the Schwann cell is in vivo.

46. The method of claim 45, wherein the Schwann cell is in a mammal with a demyelinating peripheral neuropathy.

47. The method of claim 46, wherein said inherited neuropathy is not infection-mediated.

48. The method of claim 46, wherein the mammal is human.

49. The method of claim 46, wherein the polyclonal IgG is administered locally.

50. The method of claim 49, wherein the polyclonal IgG is administered subcutaneously, intramuscularly, or intradermally.

51. The method of claim 46, wherein the polyclonal IgG is administered systemically.

52. The method of claim 51, wherein the polyclonal IgG is administered parenterally, intra-arterially, or intravenously.

53. The method of claim 46, wherein an anti-inflammatory agent is co-administered with the polyclonal IgG to the mammal.

54. The method of claim 53, wherein the anti-inflammatory agent is adrenocorticotropic hormone.

55. The method of claim 53, wherein the anti-inflammatory agent is a corticosteroid.

56. The method of claim 53, wherein the anti-inflammatory agent is an interferon.

57. The method of claim 53, wherein the anti-inflammatory agent is glatiramer acetate.

58. The method of claim 53, wherein the anti-inflammatory agent is a non-steroidal anti-inflammatory drug.

59. The method of claim 46, wherein the polyclonal IgG is administered weekly.

60. The method of claim 46, wherein the polyclonal IgG is administered biweekly.

61. The method of claim 46, wherein the polyclonal IgG is administered monthly.

62. The method of claim 46, wherein the polyclonal IgG is administered to the mammal at a dose of about 0.05 to 5 g per kg of patient body weight.

63. The method of claim 62, wherein the polyclonal IgG is administered to the mammal at a dose of about 0.5 to 2 g per kg of patient body weight.

64. A method of culturing mammalian nervous tissue which comprises axons, the method comprising contacting the tissue in culture with an effective amount of Schwann cells and an effective amount of polyclonal IgG, whereby the contacting of Schwann cells with polyclonal IgG induces upregulation of MBP genes.

* * * * *